(12) United States Patent
Cook et al.

(10) Patent No.: US 10,675,152 B2
(45) Date of Patent: Jun. 9, 2020

(54) MAGNETIC DEVICES FOR REDUCING LOADING ACROSS CARTILAGINOUS JOINTS

(71) Applicant: Fellowship of Orthopaedic Researchers, Inc., Metairie, LA (US)

(72) Inventors: Stephen D. Cook, Metairie, LA (US); Samantha L. Salkeld, Metairie, LA (US); Laura P. Patron, Belle Chase, LA (US); Liam P. Nolan, New Orleans, LA (US); Michael C. Harrison, Metairie, LA (US)

(73) Assignee: Fellowship of Orthopaedic Researchers, Inc., Metairie, LA (US)

( * ) Notice: Subject to any disclaimer, the term of this patent is extended or adjusted under 35 U.S.C. 154(b) by 54 days.

(21) Appl. No.: 16/005,641

(22) Filed: Jun. 11, 2018

(65) Prior Publication Data

US 2019/0053908 A1 Feb. 21, 2019

Related U.S. Application Data

(63) Continuation-in-part of application No. 15/835,802, filed on Dec. 8, 2017, which is a continuation-in-part of application No. 15/677,822, filed on Aug. 15, 2017.

(Continued)

(51) Int. Cl.
*A61F 2/30* (2006.01)
*A61F 2/38* (2006.01)
(Continued)

(52) U.S. Cl.
CPC .......... *A61F 2/3859* (2013.01); *A61B 17/866* (2013.01); *A61B 17/8685* (2013.01); *A61F 2/3609* (2013.01); *A61F 2/4202* (2013.01); *A61F 2/442* (2013.01); *A61B 17/863* (2013.01); *A61B 17/8625* (2013.01);
(Continued)

(58) Field of Classification Search
CPC .... A61F 2/3859; A61F 2/3609; A61F 2/4202; A61F 2/442; A61B 17/8625; A61B 2017/008976; A61B 2017/30079; A61B 2017/30153; A61B 2017/30168;
(Continued)

(56) References Cited

U.S. PATENT DOCUMENTS

| | | | | |
|---|---|---|---|---|
| 4,024,588 A | * | 5/1977 | Janssen ............ | A61F 2/30 623/18.12 |
| 5,879,386 A | * | 3/1999 | Jore ................. | A61F 2/38 623/16.11 |

(Continued)

*Primary Examiner* — Pedro Philogene
*Assistant Examiner* — David C Comstock
(74) *Attorney, Agent, or Firm* — Haug Partners LLP

(57) ABSTRACT

Methods of reducing loading across a cartilaginous joint, or of reducing pain in a cartilaginous joint caused by cartilage damage in the joint. The methods involve implanting one or more magnetic devices in the bones, or affixing one or more magnetic devices onto the surface of the bones, that form the joint. For example, to reduce loading or reduce pain in a knee joint, one or more magnetic devices maybe implanted in the femur and in the tibia. The magnetic devices are oriented to generate a repulsive magnetic force between the one or more magnetic devices of each of the bones forming the joint.

20 Claims, 20 Drawing Sheets

Related U.S. Application Data

(60) Provisional application No. 62/545,572, filed on Aug. 15, 2017.

(51) Int. Cl.
*A61F 2/44* (2006.01)
*A61F 2/36* (2006.01)
*A61F 2/42* (2006.01)
*A61B 17/86* (2006.01)
*A61B 17/00* (2006.01)

(52) U.S. Cl.
CPC .............. *A61B 2017/00455* (2013.01); *A61B 2017/00876* (2013.01); *A61F 2002/3071* (2013.01); *A61F 2002/30079* (2013.01); *A61F 2002/30153* (2013.01); *A61F 2002/30168* (2013.01); *A61F 2002/30224* (2013.01); *A61F 2002/30261* (2013.01)

(58) Field of Classification Search
CPC .......... A61B 2017/30224; A61B 2017/30261; A61B 2017/30713

USPC ..... 606/279; 623/11.11, 16.11, 17.11, 18.11, 623/18.12, 20.14, 20.21, 23.39, 23.53, 623/23.71

See application file for complete search history.

(56) References Cited

U.S. PATENT DOCUMENTS

| | | | | |
|---|---|---|---|---|
| 2002/0032484 | A1* | 3/2002 | Hyde, Jr. | A61B 17/68 623/18.12 |
| 2004/0059423 | A1* | 3/2004 | Barnes | A61B 17/58 623/18.12 |
| 2007/0100457 | A1* | 5/2007 | Hyde, Jr. | A61B 17/88 623/18.12 |
| 2011/0257754 | A1* | 10/2011 | Fleischmann | A43B 1/0054 623/18.12 |
| 2017/0231768 | A1* | 8/2017 | Gross | A61B 17/56 623/18.12 |
| 2019/0021776 | A1* | 1/2019 | Archbold | A61B 17/8605 |

* cited by examiner

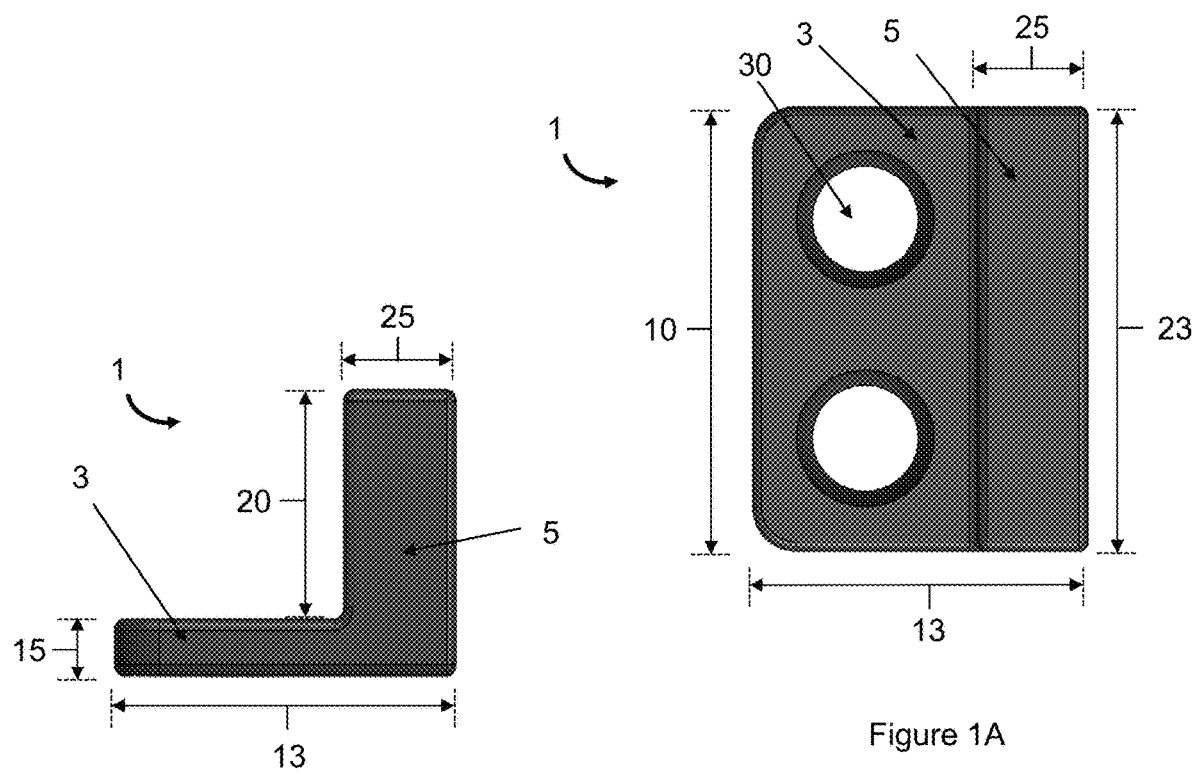
Figure 1A
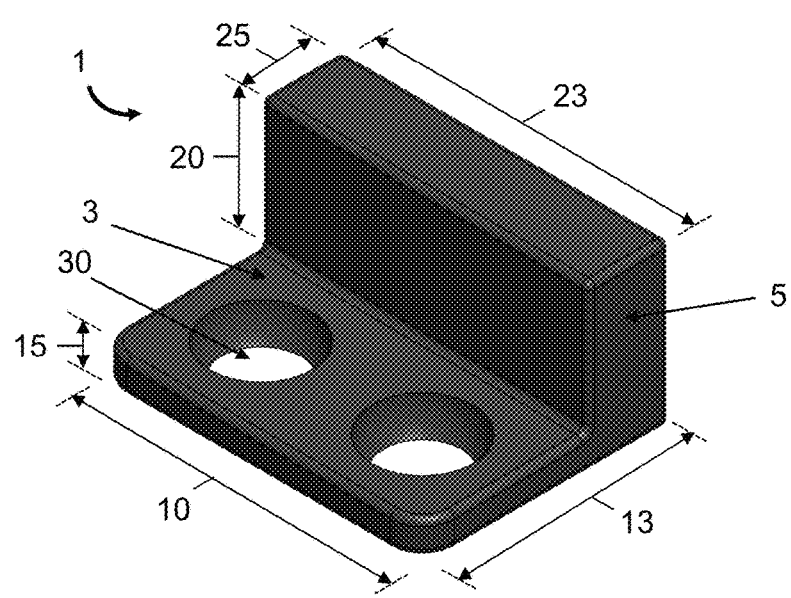
Figure 1B
Figure 1C

MAGNETIC DEVICES FOR REDUCING LOADING ACROSS CARTILAGINOUS JOINTS

CROSS-REFERENCE TO RELATED APPLICATIONS

This application is a continuation-in-part of U.S. patent application Ser. No. 15/835,802, filed on Dec. 8, 2017, which is a continuation-in-part of U.S. patent application Ser. No. 15/677,822, filed on Aug. 15, 2017, which claims the benefit of U.S. Provisional Application Ser. No. 62/545,572, filed on Aug. 15, 2017, which are all hereby incorporated by reference in its entirety.

BACKGROUND OF THE INVENTION

Cartilage and other connective tissue in cartilaginous joints can break, fracture, or otherwise become damaged due to injury, age, heredity, or combinations thereof, resulting in pain and/or loss of motion. Often, treatments for such conditions are ineffective in alleviating the pain, or require a long recovery.

For example, hyaline cartilage that covers the surface of bones forming a load-bearing joint allows pain free motion at the joint and absorbs loads placed across the joint during activities of daily living. But these cartilage surfaces can experience wear and damage due to trauma or osteoarthritis, or other factors such as obesity and poor joint surface alignment, and the exposed bone surfaces can cause significant pain in the joint upon motion. Moreover, the loss of the cartilage surface can diminish its shock absorption capability, which can result in excessive loads being placed across the joint and lead to further damage to the cartilage surfaces and increasing patient symptoms. Reducing load across the joint is an effective way clinically of reducing the level of pain in the patient, and can be accomplished by several methods, including weight loss, surgery to realign the anatomy, and, in cases of severe cartilage loss or wear, replacement of the joint. However, weight loss may be difficult or slow to achieve, and it may take time before it results in a reduction in load or alleviation of pain. Further, surgery or joint replacement does not leave the joint intact and requires a long recovery time.

As another example, cartilage and components of the intervertebral disc between vertebrae can degenerate, resulting in pain and pressure on the spinal cord. Traction methods are meant to relax the soft tissue and separate spinal vertebral segments, therefore creating negative intra-disc pressure, retracting bulging discs, and removing impingements on nerves. However, while methods and devices for supplying traction forces are generally known, they do not provide consistent, continuous low magnitude traction forces in order to maintain disc height and health and to relieve acute and chronic cervical neck pain. In addition, current apparatuses and methods for fixation or fusion of bones and joints to promote healing, relieve pain, and/or reduce future injury of other cartilaginous joints are often insufficient to provide proper stability or otherwise aid in healing or treating the bones and connective tissues involved.

Thus, there remains a need in the art for an intervention that effectively reduces loading in cartilaginous joints and that does not substantially alter the anatomy of the joint, thereby requiring a more effective treatment and shorter time to recover.

SUMMARY OF INVENTION

In one aspect, the present invention relates to methods of reducing loading across a cartilaginous joint. In another aspect, the invention relates to methods of reducing pain in a cartilaginous joint caused by cartilage damage in the joint. These methods comprise implanting one or more magnetic devices in the bones that form the joint, in which the magnetic devices are oriented to generate a repulsive magnetic force between the magnetic devices in each of the bones.

In embodiments of the invention, the cartilaginous joint is a knee joint and the method comprises implanting one or more magnetic devices in the distal femur and one or more magnetic devices in the proximal tibia, wherein the one or more magnetic devices in the femur and the one or more magnetic devices in the tibia are oriented to generate a repulsive magnetic force therebetween. In some embodiments, the one or more magnetic devices in the femur are implanted in a condyle of the femur. In certain embodiments, the one or more magnetic devices in the femur are implanted in the lateral condyle of the femur, such as implanted into the lateral surface of the lateral condyle. In other embodiments, the one or more magnetic devices in the femur are implanted in the medial condyle of the femur, such as implanted into the medial surface of the medial condyle. In certain embodiments, the one or more magnetic devices in the femur are implanted in both the lateral condyle and the medial condyle of the femur.

In some embodiments of the invention, the one or more magnetic devices in the tibia are implanted in a condyle of the tibia. In certain embodiments, the one or more magnetics devices in the tibia are implanted in the lateral condyle of the tibia, such as implanted into the lateral surface of the lateral condyle. In other embodiments, the one or more magnetic devices in the tibia are implanted in the medial condyle of the tibia, such as implanted into the medial surface of the medial condyle. In certain embodiments, the one or more magnetic devices in the tibia are implanted in both the lateral condyle and the medial condyle of the tibia.

In some embodiments, the one or more magnetic devices in the femur are implanted in the lateral condyle of the femur, and the one or more magnetic devices in the tibia are implanted in the lateral condyle of the tibia. In certain embodiments, the one or more magnetic devices in the femur are implanted in the medial condyle of the femur, and the one or more magnetic devices in the tibia are implanted in the medial condyle of the tibia.

In some embodiments, the number of magnetic devices implanted in the femur may range from one to five, i.e., one, two, three, four, or five magnetic devices. In some embodiments, the number of magnetic devices implanted in the tibia may range from one to five, i.e., one, two, three, four, or five magnetic devices. In certain embodiments, the number of magnetic devices implanted in the femur may be the same as the number of magnetic devices implanted in the tibia. In other embodiments, the number of magnetic devices implanted in the femur may be different than the number of magnetic devices implanted in the tibia.

In embodiments of the invention, the magnetic devices are implanted in a configuration such that the one or more magnetic devices of the femur are maintained at a prescribed distance, or a range of distances, from the one or more magnetic devices of the tibia while the knee undergoes flexion and/or extension. In some embodiments, the magnetic devices are implanted in a curved configuration generally along an anatomic curve of the condyle of the femur and/or tibia. For instance, the magnetic devices are implanted into the lateral surface of the lateral condyle of the femur and/or tibia in a configuration generally along the anterior-posterior curve of the surface of the lateral condyle of the femur and/or tibia. Alternatively or in addition, the magnetic devices are implanted into the medial surface of the medial condyle of the femur and/or tibia in a configuration generally along the anterior-posterior curve of the surface of the medial condyle of the femur and/or tibia. In other embodiments, the magnetic devices are implanted in a linear configuration.

In embodiments of the invention, the cartilaginous joint is an acetabulofemoral joint and the method comprises implanting one or more magnetic devices in the proximal femur and one or more magnetic devices in the hip bone adjacent to the acetabulum, wherein the one or more magnetic devices in the femur and the one or more magnetic devices in the hip bone are oriented to generate a repulsive magnetic force therebetween. In some embodiments, the one or more magnetic devices in the femur are implanted in the femoral head.

In embodiments of the invention, the cartilaginous joint is an ankle joint and the method comprises implanting one or more magnetic devices in the distal tibia and/or fibula and one or more magnetic devices in the talus, wherein the one or more magnetic devices in the tibia and/or fibula and the one or more magnetic devices in the talus are oriented to generate a repulsive magnetic force therebetween. In some embodiments, one or more magnetic devices are implanted in both the tibia and the fibula. In other embodiments, one or more magnetic devices are implanted in the tibia only. In certain embodiments, one or more magnetic devices are implanted in the proximal talus. In some embodiments, the magnetic device(s) are implanted into the medial surface of the tibia and/or fibula and into the medial surface of the talus. In other embodiments, the magnetic device(s) are implanted into the lateral surface of the tibia and/or fibula and into the lateral surface of the talus. In yet other embodiments, the magnetic device(s) are implanted into both the medial surface and lateral surface of the tibia and/or fibula and into both the medial surface and lateral surface of the talus.

In embodiments of the invention, the cartilaginous joint is an intervertebral joint and the method comprises implanting one or more magnetic devices in a first vertebra that is superior to the intervertebral joint and implanting one or more magnetic devices in a second vertebra that is inferior to the intervertebral joint, wherein the one or more magnetic devices in the first vertebra and the one or more magnetic devices in the second vertebra are oriented to generate a repulsive magnetic force therebetween. In some embodiments, the one or more magnetic devices are implanted in the vertebral body of the first and the second vertebra.

An aspect of the invention relates to (i) methods of providing cervical traction to reduce pain in an intervertebral joint of a first vertebra superior to the joint and a second vertebra inferior to the joint, (ii) methods of treating pain caused by a herniated disk between a first vertebra that is superior to the herniated disk and a second vertebra that is inferior to the herniated disk, and (iii) methods of treating a herniated disk between a first vertebra that is superior to the herniated disk and a second vertebra that is inferior to the herniated disk. In embodiments of the invention, the method comprises implanting one or more magnetic devices, such as at least two magnetic devices, in the first vertebra, and implanting one or more magnetic devices, such as at least two magnetic devices, in the second vertebra. The one or more magnetic devices in the first vertebra and the one or more magnetic devices in the second vertebra are oriented to generate a repulsive magnetic force therebetween.

In embodiments of the invention, each magnetic device comprises a magnet enclosed within an outer casing. The magnetic device may be generally any geometric shape, such as a cylinder, disc, prism, cone, and pyramid. In certain embodiments, the magnetic device may be a bone screw that comprises a magnet.

In some embodiments, the magnets in the magnetic device have a radial magnetic orientation. In certain embodiments, the magnets have an axial or off-axial magnetic orientation.

In some embodiments, the casing of the magnetic implant may comprise a mark that indicates the direction of the pole magnetization of the magnet inside of the casing.

In alternative embodiments, the methods of the present invention comprise affixing one or more magnetic devices onto the surface of the bones that form the cartilaginous joint. For instance, one or more magnetic devices may be affixed to the surface of the distal femur and one or more magnetic devices onto the surface of the proximal tibia, wherein the one or more magnetic devices on the surface of the distal femur and the one or more magnetic devices on the surface of the proximal tibia are oriented to generate a repulsive magnetic force therebetween. The magnetic device(s) may be affixed to the lateral surface, the medial surface, or both the lateral and medial surfaces, of the distal femur and the proximal tibia.

BRIEF DESCRIPTION OF THE DRAWING FIGURES

The present disclosure will be further explained with reference to the attached drawing figures, wherein like structures are referred to by like numerals throughout the several views. The drawing figures shown are not necessarily to scale, with emphasis instead generally being placed upon illustrating the principles of the present disclosure, and some features may be exaggerated to show details of particular components. In addition, any measurements, specifications, and the like shown in the drawing figures, or described below, are intended to be illustrative, and not restrictive. Therefore, specific structural and functional details disclosed herein are not to be interpreted as limiting, but merely as a representative basis for teaching one skilled in the art to variously employ the magnetic devices and methods of their use.

FIGS. 1A, 1B, and 1C are different views of a magnetic device having the shape of a plate attached to a casing that encloses a magnet, according to embodiments of the present invention. FIG. 1A is a top view of magnetic device, FIG. 1B is a side view of the magnetic device, and FIG. 1C is a prospective view of the magnetic device.

FIG. 5A is a top view of a bone screw, and FIG. 5B is a cross-sectional bottom view of a bone screw.

FIG. 6A is an exploded view of a disc-shaped housing, and FIG. 6B is a side view of a disc-shaped housing.

FIG. 7A is a lateral view of the knee joint, and FIG. 7B is an anterior view of the knee joint.

FIG. 8A is a lateral view of the knee joint, and FIG. 8B is an anterior view of the knee joint.

FIG. 9A is a lateral view of the knee joint, and FIG. 9B is an anterior view of the knee joint.

FIG. 10A is a lateral view of the knee joint, and FIG. 10B is an anterior view of the knee joint.

FIG. 11A is a lateral view of the knee joint, and FIG. 11B is an anterior view of the knee joint.

Figure 12A:
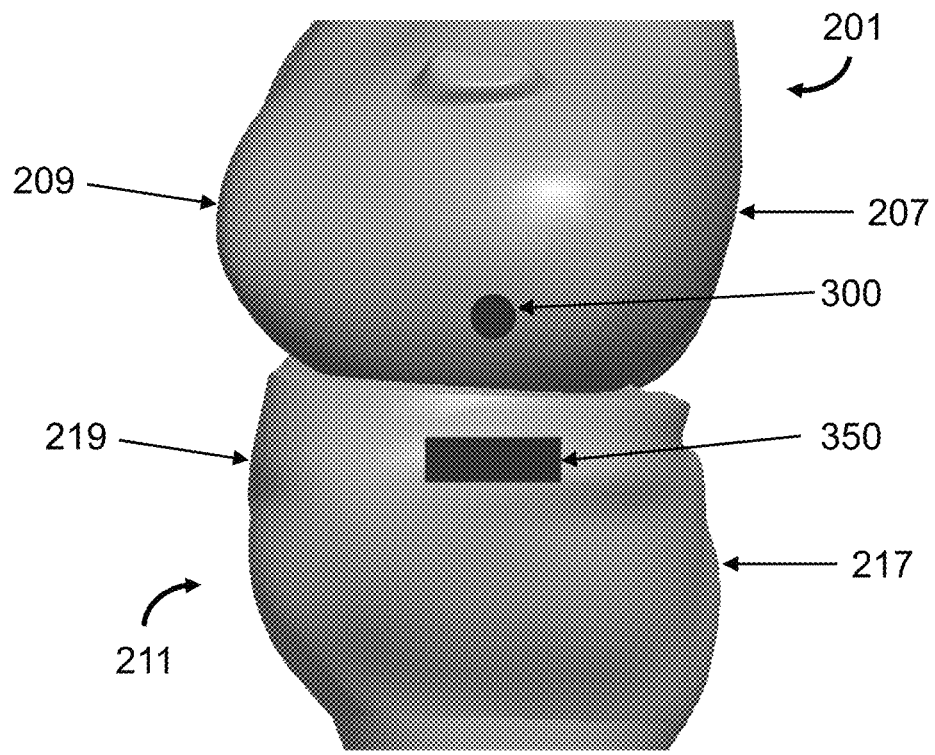
Figure 12B:
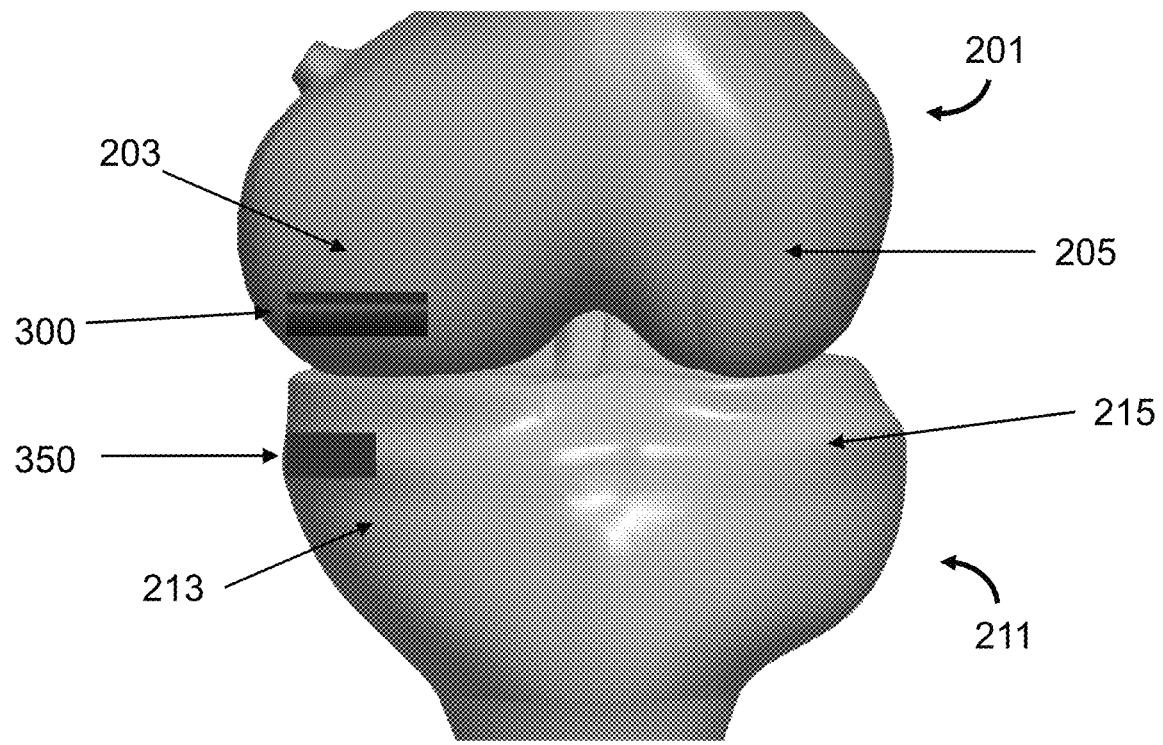

FIGS. 12A and 12B are different views of a knee joint at 0° flexion with a cylindrical magnetic device implanted into the lateral surface of the lateral condyle of the femur and a rectangular prism-shaped magnetic device implanted into the lateral surface of the lateral condyle of the tibia, according to embodiments of the present invention. FIG. 12A is a lateral view of the knee joint, and FIG. 12B is an anterior view of the knee joint.

Figure 13A:
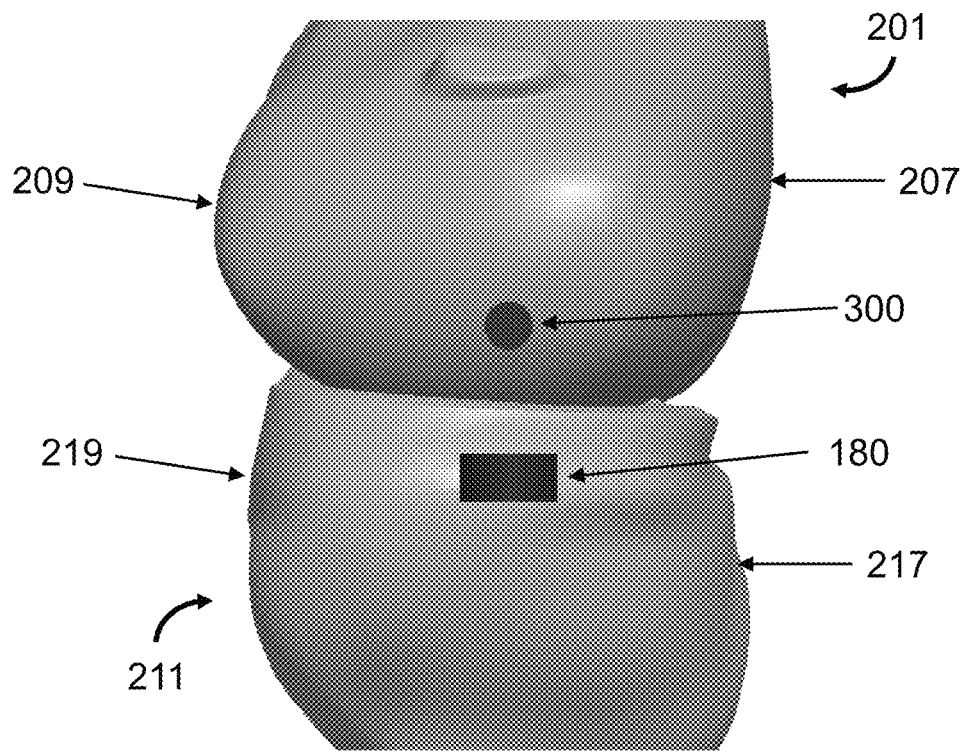
Figure 13B:
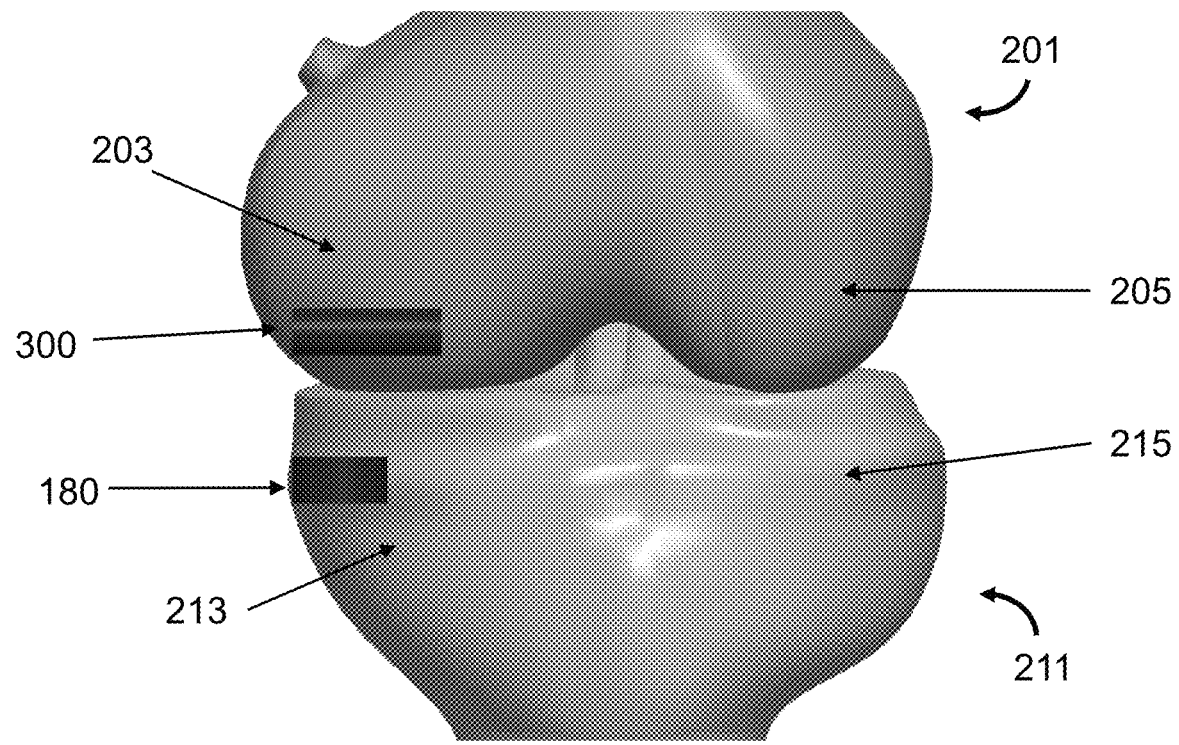

FIGS. 13A and 13B are different views of a knee joint at 0° flexion with a cylindrical magnetic device implanted into the lateral surface of the lateral condyle of the femur and a disc-shaped magnetic device implanted into the lateral surface of the lateral condyle of the tibia, according to embodiments of the present invention. FIG. 13A is a lateral view of the knee joint, and FIG. 13B is an anterior view of the knee joint.

Figure 14A:
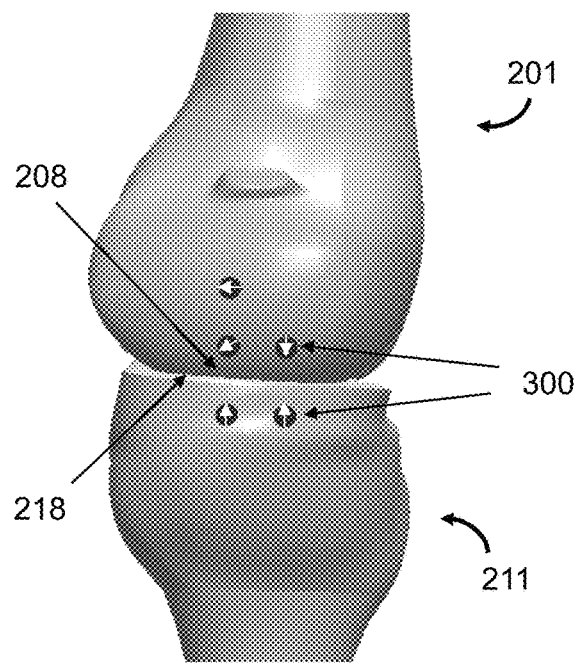
Figure 14B:
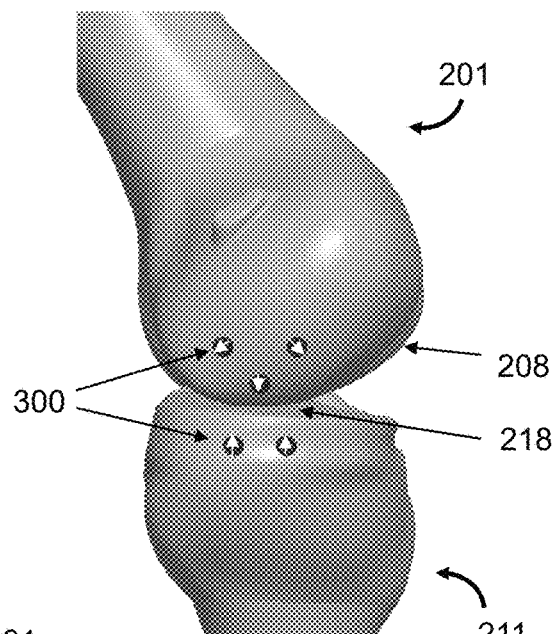
Figure 14C:
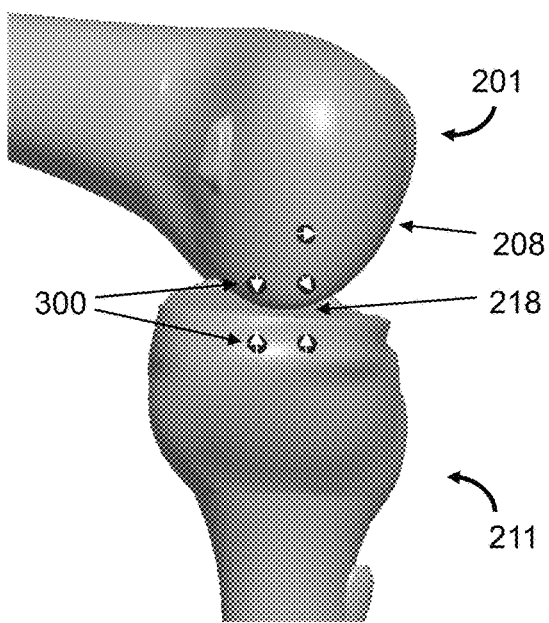

FIGS. 14A, 14B, and 14C are lateral views of a knee joint at different angles of flexion, in which cylindrical magnetic devices are implanted into the lateral surface of the lateral condyle of the femur and the tibia, according to embodiments of the present invention. FIG. 14A is a lateral view of the knee joint at 0° flexion, FIG. 14B is a lateral view of the knee joint at 45° flexion, and FIG. 14C is a lateral view of the knee joint at 90° flexion. The arrows in the magnetic devices represent north pole direction.

Figure 15A:
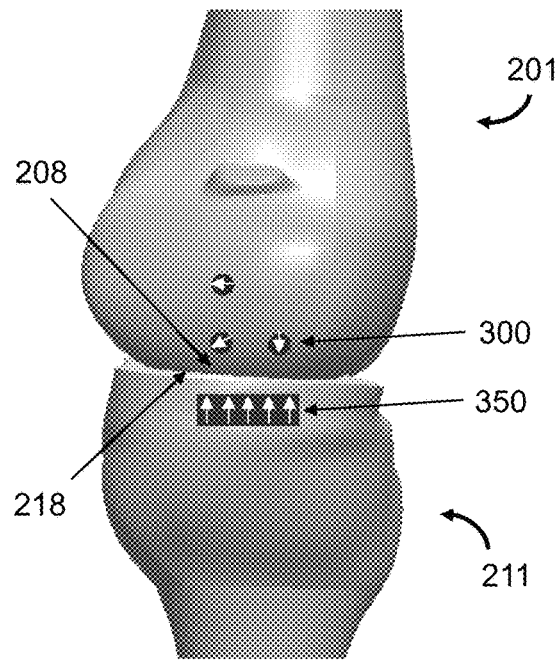
Figure 15B:
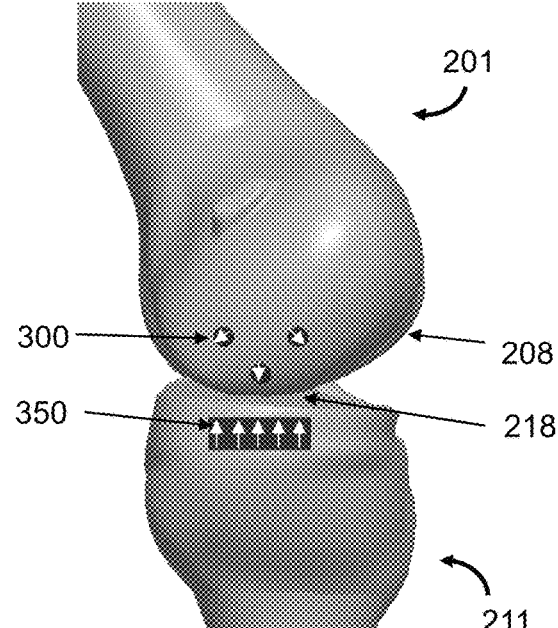
Figure 15C:
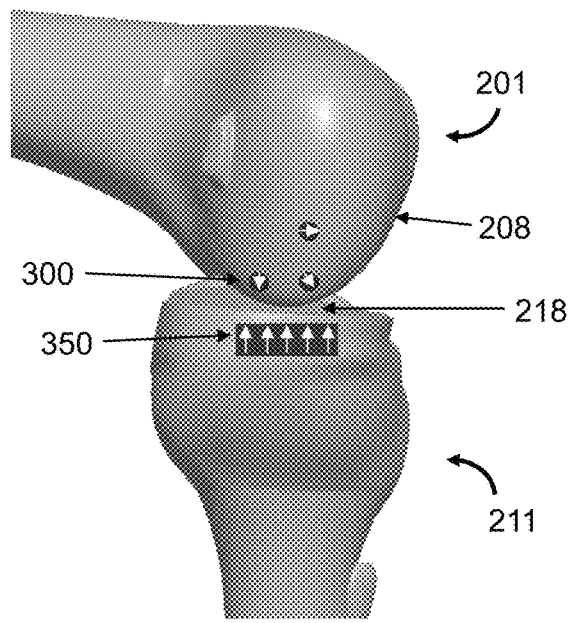

FIGS. 15A, 15B, and 15C are lateral views of a knee joint at different angles of flexion, in which cylindrical magnetic devices are implanted into the lateral surface of the lateral condyle of the femur and a rectangular prism-shaped magnetic device is implanted into the lateral surface of the lateral condyle of the tibia, according to embodiments of the present invention. FIG. 15A is a lateral view of the knee joint at 0° flexion, FIG. 15B is a lateral view of the knee joint at 45° flexion, and FIG. 15C is a lateral view of the knee joint at 90° flexion. The arrows in the magnetic devices represent north pole direction.

Figure 16A:
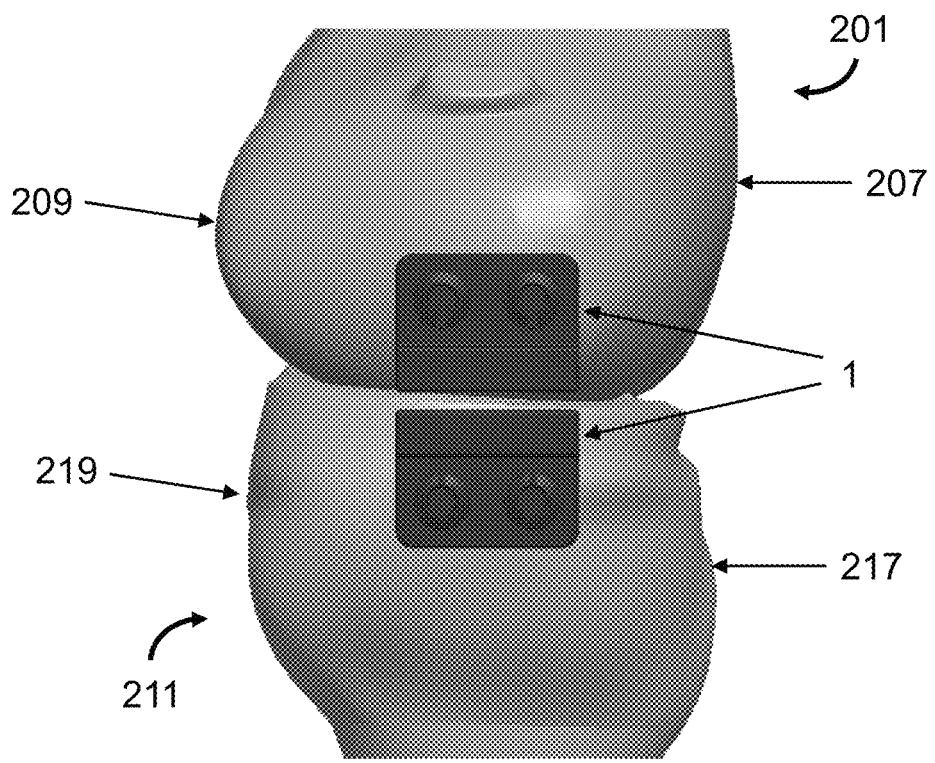
Figure 16B:
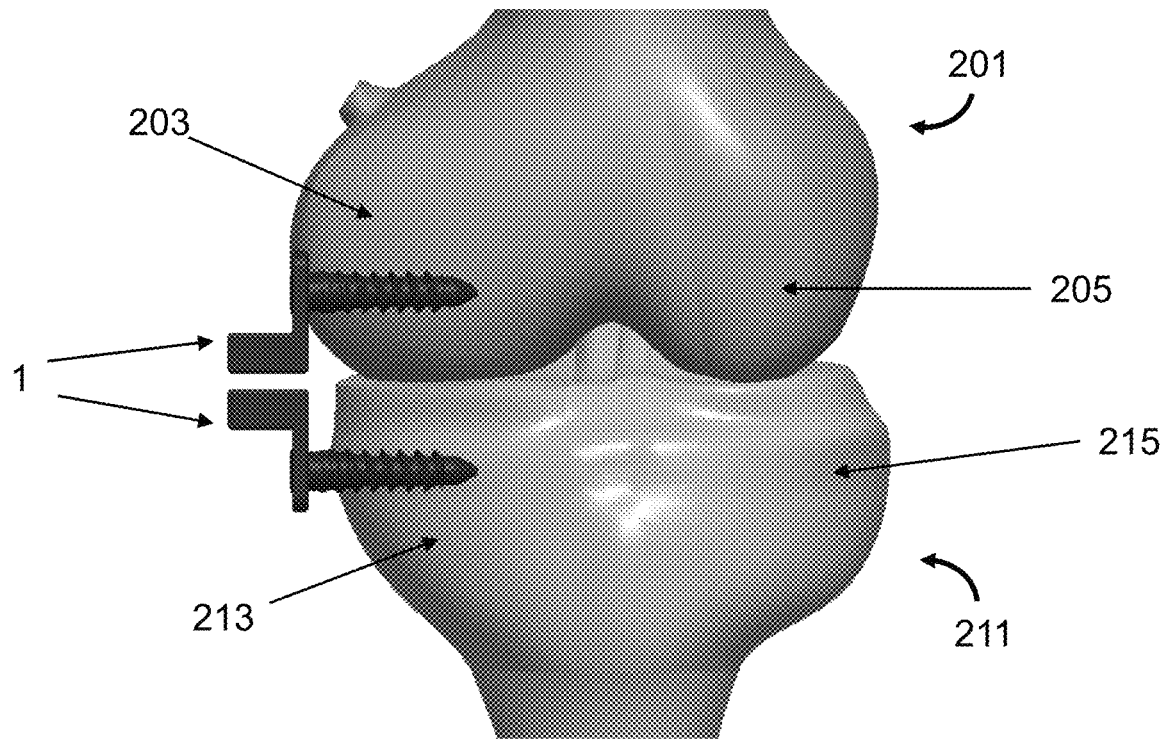

FIGS. 16A and 16B are different views of a knee joint at 0° flexion with magnetic devices affixed to the lateral surface of the lateral condyle of the femur and tibia, in which the magnetic devices have the shape of a plate attached to a casing that encloses a magnet, according to embodiments of the present invention. FIG. 16A is a lateral view of the knee joint, and FIG. 16B is an anterior view of the knee joint.

Figure 17A:
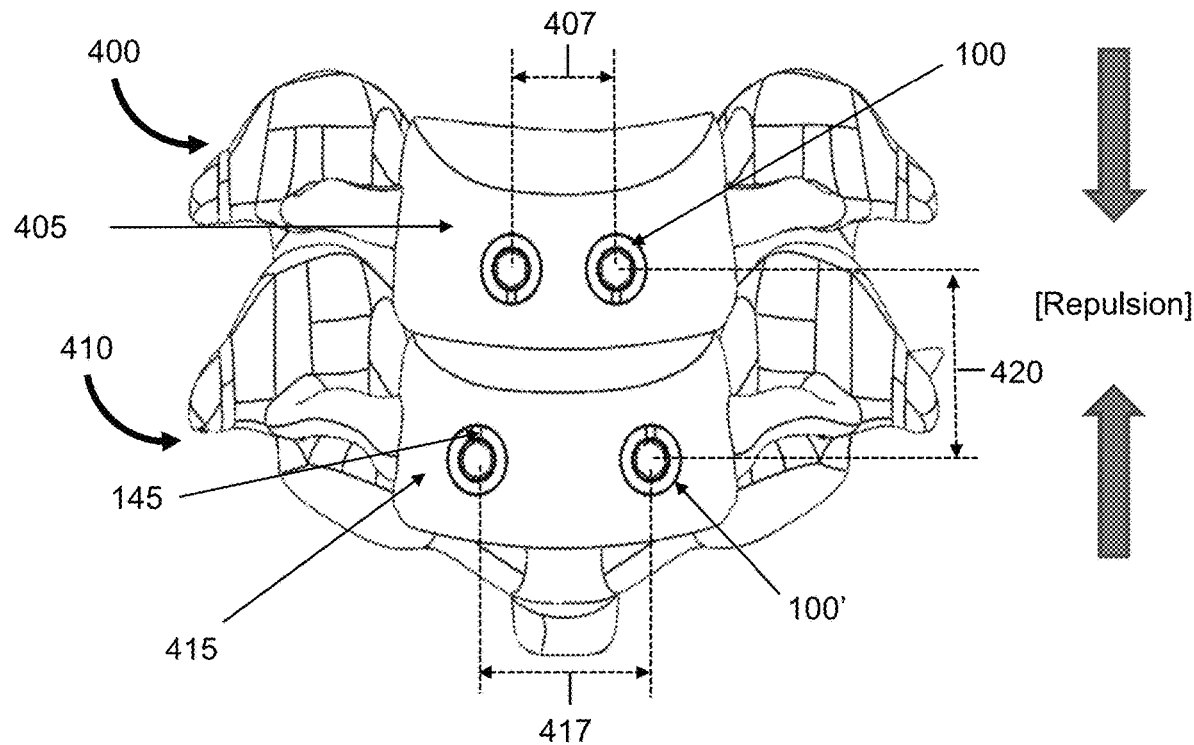
Figure 17B:
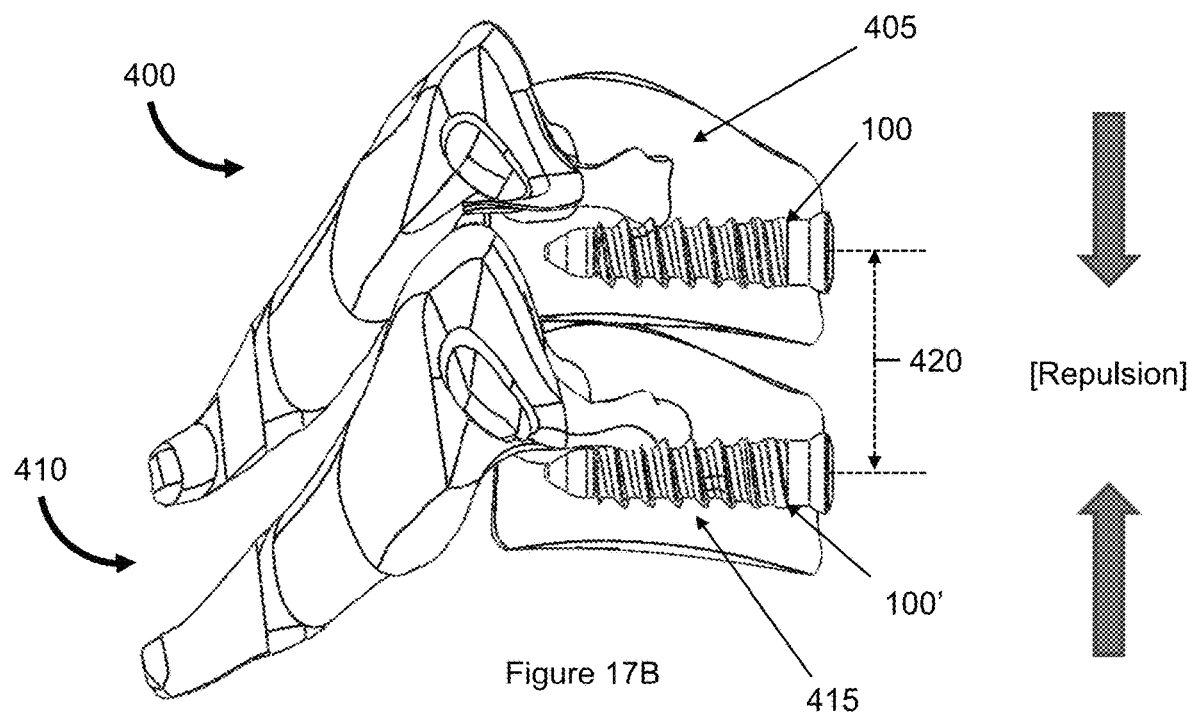

FIGS. 17A and 17B are different views of an intervertebral joint with bone screw magnetic devices implanted in a vertebra superior to the joint and in a vertebra inferior to the joint, according to embodiments of the present invention. FIG. 17A is an anterior view of the intervertebral joint, and FIG. 17B is a lateral view of the intervertebral joint.

Figure 18A:
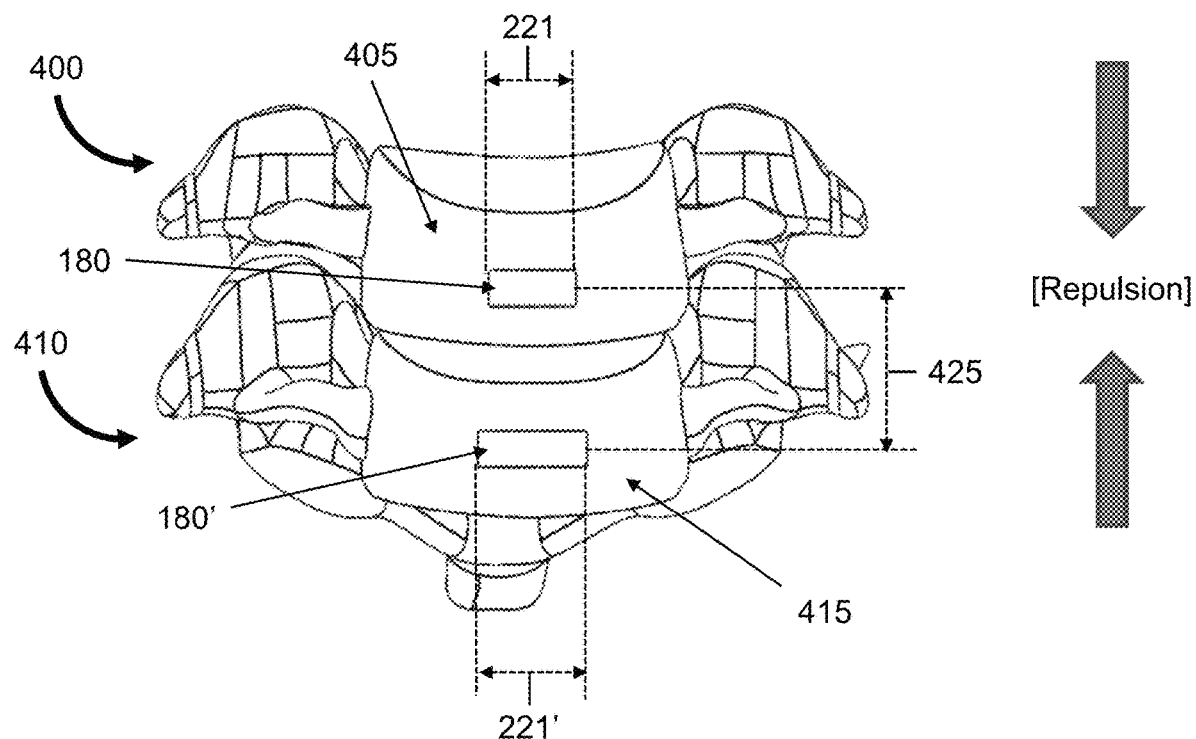
Figure 18B:
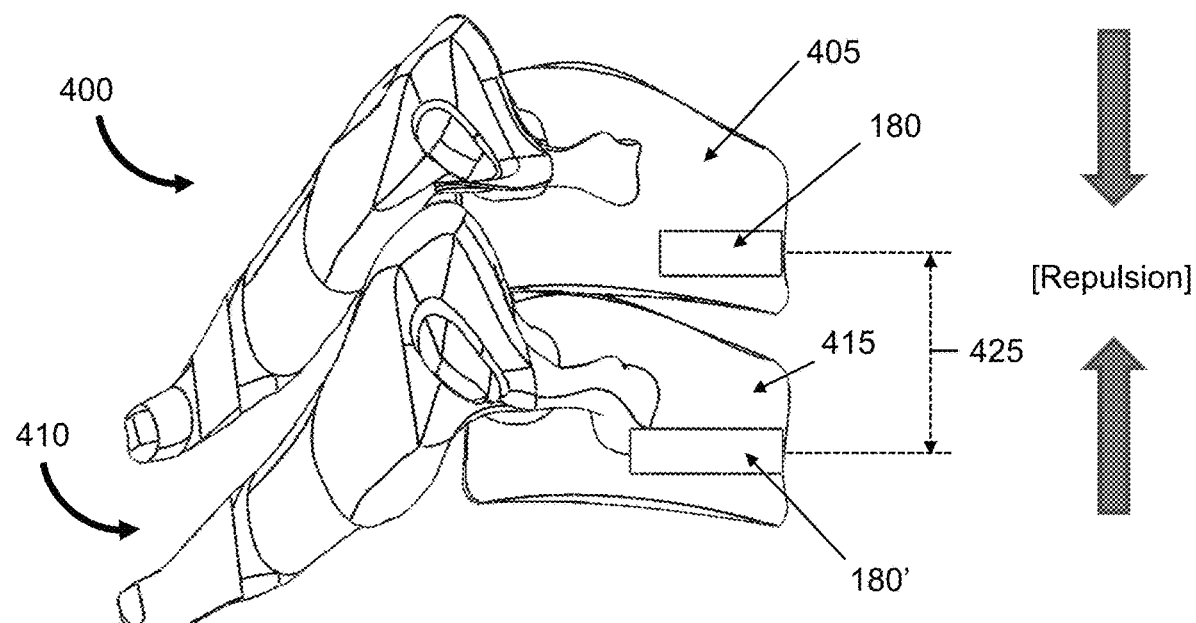

FIGS. 18A and 18B are different views of an intervertebral joint with disc-shaped magnetic devices implanted in a vertebra superior to the joint and in a vertebra inferior to the joint, according to embodiments of the present invention. FIG. 18A is an anterior view of the intervertebral joint, and FIG. 18B is a lateral view of the intervertebral joint.

Figure 19A:
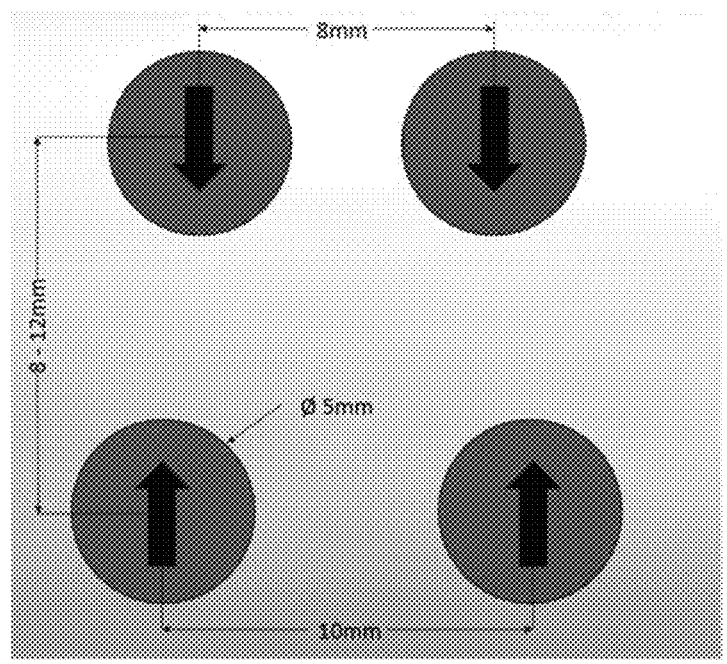
Figure 19B:
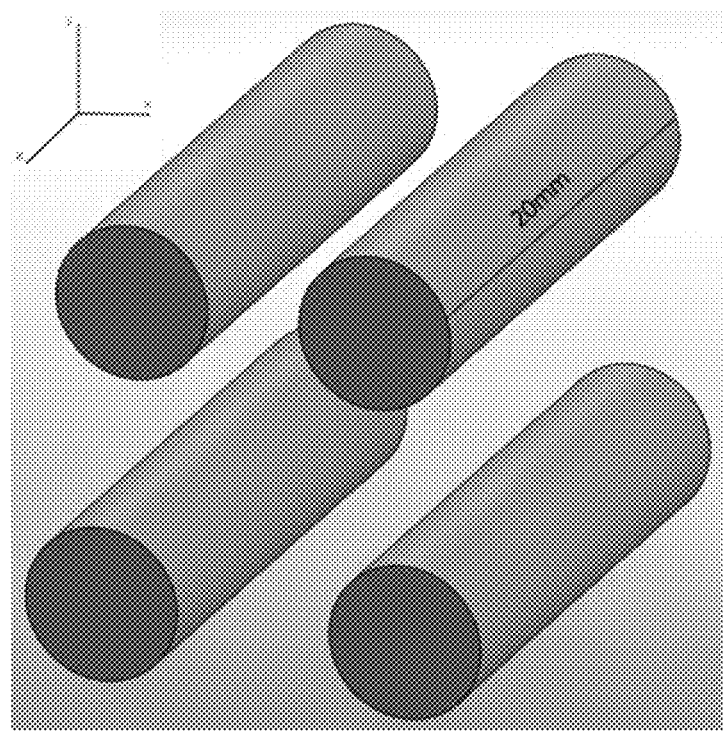

FIGS. 19A and 19B are views of the magnet configuration studied in Example 2.

DETAILED DESCRIPTION OF THE INVENTION

This invention provides a surgically implanted device for partially unloading a cartilaginous joint, thereby reducing the loading and resulting stress across the cartilage in the joint, including the cartilage on the bone surfaces. Unloading of the joint may be accomplished by implanting magnetic devices into or onto the bones that form the joint. The anatomy of the internal joint remains intact. The repulsive forces generated by alignment of the magnetic fields of the devices act to reduce the load across the joint, including during activities. Without being bound by theory, the reduction in load across the joint reduces contact stresses (pressures) on the joint surfaces, resulting in less pain in the patient. The reduction of load also prevents excessive forces from causing further damage to the cartilage surfaces and joint. In cases in which the joint is an intervertebral joint, the repulsive forces can cause traction, and therefore can be used as a treatment for a herniated disk and/or reduce pain across the joint.

Magnetic Devices

The magnetic devices used with the methods of the invention comprise a magnet enclosed within a casing. The casing may comprise a titanium alloy or other type of acceptable biomaterial that is known in the art. The magnet may be hermetically sealed within the casing. In some embodiments, the casing may comprise two or more components (e.g., an upper component and a lower component), in which the two or more components may be laser-welded together in order to create a hermetically-sealed environment for the magnet.

The casing comprises an outer surface that, upon implantation, will face the biological environment, and an inner surface that faces the magnet. The outer surface may be smooth or may comprise surface modifications that stabilize and/or prevent movement, such as rotation, of the device once it is implanted. In some embodiments, the surface modifications may adhere the magnetic device to the biological environment or may generate friction between the magnetic device and the biological environment. The surface modifications may comprise a roughened surface or a pattern of protrusions that are raised from the surface. The surface modifications may also comprise screw thread(s) or a grooved design, such as in embodiments in which the casing is a bone screw, or any other acceptable surgical configuration.

The magnetic device may be generally any geometric shape, such as a cylinder, disc, prism (including rectangular prism, hexagonal prism, triangular prism, cube, etc.), cone, and pyramid. In some embodiments, the magnetic device may comprise a bone screw.

The shape of the magnetic device may be primarily determined by the shape of the casing. In some embodiments, the magnet of the magnetic device may comprise the same general shape as the casing. For example, if the casing is cylindrical, the magnet within the casing may also be generally cylindrical; if the casing is disc-shaped, the magnet within the casing may also be generally disc-shaped. In embodiments in which the casing is in the form of a bone screw, the magnet within the casing may be cylindrical. In embodiments in which the casing is shaped like an arc, such as if the casing were attached to a plate, the magnet within the casing may also be in the shape of an arc.

The magnetic device may comprise a size appropriate for the bone in which it is being implanted and for generating the desired reduction in force across the joint. For example, cylindrical magnetic devices may have a diameter of about 2 mm to about 20 mm, or about 3 mm to about 15 mm, or about 4 mm to about 10 mm; and a length of about 3 mm to about 100 mm, or about 5 mm to about 40 mm, or about 10 mm to about 30 mm, or about 15 mm to about 25 mm. The size of the cylindrical magnetic device may also depend on the bone in which the device is being implanted. For example, in some embodiments, cylindrical magnetic devices may comprise: (i) for implantation in a femur, a diameter of about 4 mm to about 15 mm and a length of about 10 mm to about 30 mm; (ii) for implantation in a tibia, a diameter of about 3 mm to about 10 mm and a length of about 15 mm to about 25 mm; (iii) for implantation in cervical vertebrae, a diameter of about 3.5 mm to about 6 mm and a length of about 8 mm to about 100 mm; and (iv) for implantation in lumbar vertebrae, a diameter of about 4 mm to about 10 mm and a length of about 15 mm to about 40 mm.

As another example, disc-shaped magnetic devices may comprise a circular diameter of about 8 mm to about 40 mm, or about 12 mm to about 30 mm, and a height of about 2 mm to about 15 mm, or about 3 mm to about 10 mm. Rectangular prism-shaped magnetic devices may comprise a length, width, and height of about 5 mm to about 40 mm, or about 12 mm to about 30 mm.

The magnet within the casing may comprise materials known in the art. For example, the magnet may be iron-based, nickel-based, cobalt-based, or an alloy of rare-earth metals. In certain embodiments, the magnet may be a rare-earth magnet, which generally has strong attraction and repulsion forces and has high retentive capacity and resistance to demagnification. In a preferred embodiment, the rare-earth magnet is an alloy of neodymium, iron, and boron ("NdFeB"). NdFeB magnets may provide strong permanent magnetism, high retentive capacity, and resistance to demagnetization.

The casing or the plate may be fabricated with a metal alloy known in the art for orthopaedic applications, for example, titanium, cobalt chromium, or stainless steel. In certain embodiments, the casing or plate may comprise a polymer, such as polyetheretherketone (PEEK) or polyurethane, or a combination thereof. In alternative embodiments, the casing or plate may comprise composites of polymers and fibers, such as carbon fiber-reinforced PEEK.

The magnet may be magnetized in a radial, axial, or off-axial direction. The magnetic field generated by the magnets may be of any geometric shape, including disc-shaped, circular, rectangular, oval, ellipsoid (with an axial magnetic orientation), etc. In certain embodiments, cylindrical magnetic devices are magnetized in a radial direction. In some embodiments, disc-shaped magnetic devices are magnetized in an axial direction.

The direction of the pole magnetization of the magnet inside of the casing may be indicated by a mark on the outer surface of the casing. The mark may be a different color or shade than the color of rest of the outer surface of the casing, such as a dark-colored mark; in such a case, the mark may be created, for instance, using laser-etching. The mark may also be a physical feature on the outer surface of the casing, such as a notch or a raised groove.

Plates

In some embodiments, the magnetic device may be in the shape of a plate attached to a casing that encloses the magnet. FIGS. 1A, 1B, and 1C show a magnetic device 1 in the shape of a plate 3 with a casing 5 that encases the magnet (not shown). The plate 3 in combination with the casing 5 forms a shape resembling the letter "L," with the plate 3 as the horizontal line of the letter and the casing 5 as the vertical line. The plate 3 aspect of the magnetic device 1 may have a length 10 of about 8 mm to about 40 mm, or about 12 mm to about 30 mm; a width 13 of about 5 mm to about 30 mm, or about 8 mm to about 25 mm; and a height 15 of about 1 mm to about 15 mm, or about 2 mm to about 10 mm. The casing 5 encasing the magnet may be in the shape of a rectangular prism that extends from the surface of the plate 3 by a height 20 of about 1 mm to about 25 mm, or about 2 mm to about 20 mm. The length 23 of the casing may be the same as the length 10 of the plate 3 (see FIGS. 1A, 1B, and 1C), and the width 25 of the casing 5 may be about 1 mm to about 25 mm, or about 2 mm to about 20 mm. The magnetic device 1 may also comprise one or more apertures 30 on the plate 3 that are configured to receive a bone screw or the like. For example, the one or more apertures 30 may be circular and of a diameter appropriate for bone screws known in the art. The number of apertures may vary depending on the type of bone to which the device is being affixed, and is typically from 1 to 6 apertures, i.e., 1, 2, 3, 4, 5, or 6 apertures.

Bone Screws

In some embodiments, the magnetic device may be a bone screw. With reference to FIGS. 2, 3, 4, 5A, and 5B, in certain embodiments, bone screw 100 may comprise a shaft 101 having an upper section 105, a middle section 110, and a lower section 115. The shaft 101 may comprise a cross-section that is generally circular.

The shaft 101 may comprise an outer wall 120, onto which there are a plurality of threads 122. The threads 122 may have a pitch, depth, and shape that are known in the art for threads of orthopaedic screws, including cortical and cancellous screws. For example, the threads may have any shape as known in the art for drilling into bone, including but not limited to V-thread, buttress thread, reverse buttress, and square thread.

The upper section 105 of the shaft 101 may also be considered as the head of the screw 100. The top surface 107 of the upper section 105 may comprise a drive 140 that is configured for insertion of a driver, such as 2.5 mm tapered hex driver. The drive 140 may also be configured for insertion of other types of drivers, for instance, Philips-head drivers or flat-head drivers.

The shaft 101 may comprise an inner wall surface 125 that is a result of, or is defined by, a bore 130. The bore 130 may be located generally throughout the entire middle section 110 of the shaft 101. A magnet 135 may be housed in the bore 130, and may be entirely encased within the shaft 101, including by the outer wall 120 and by the lower section 115. In certain embodiments, the bore 130 may be generally cylindrical in shape, and therefore the magnet 135 in the bore 130 also may be generally cylindrical in shape. Other shapes are also envisioned for the magnet. For example, the magnet may be ring-shaped, i.e., the magnet itself may comprise a bore through its center along the long axis of the magnet.

The magnet 135 may be prevented from rotating inside the bore 130. In some embodiments, the bore 130 may be generally cylindrical in shape but with at least one flattened side 150, and consequently the magnet 135 in the bore 130 also may be generally cylindrical in shape, but with a flattened side 137. In other embodiments, the bore 130 may be generally cylindrical in shape but may have more than one flattened side, and the magnet 135 in the bore 130 may also be generally cylindrical in shape but may have more than one flattened side (not shown). Alternatively, the magnet 135 may be prevented from rotating inside the bore 130 by gluing or laser welding the magnet 135 to one or more portions of the inner wall surface 125 of the shaft 101. For example, the magnet may be glued in place with a surgical adhesive such as medical grade epoxy. As yet another alternative, the magnet 135 may be tapered to generate a press fit within the bore 130 of the shaft 101 (not shown).

The magnet 135 may comprise materials known in the art. For example, the magnet 135 may be iron-based, nickel-based, cobalt-based, or an alloy of rare-earth metals. In certain embodiments, the magnet 135 may be a rare-earth magnet. In a preferred embodiment, the rare-earth magnet is NdFeB.

The magnet 135 may be magnetized in the radial or axial direction. In some embodiments, the orientation, i.e., the direction of the pole magnetization, of the magnet 135 inside of the bore 130 may be indicated by a mark 145 on the top surface 107 of the upper section 105 of the screw 100. The mark 145 may be a different color or shade than the color of rest of the upper section 105 of the screw 100, e.g., a dark-colored mark; in such a case, the mark 145 may be created, for instance, using laser-etching. The mark 145 may also be a physical feature on the top surface 107 of the upper section 105 of the screw 100, such as a notch or a raised groove.

The shaft 101 may be fabricated with a metal alloy known in the art for orthopaedic applications, for example, titanium, cobalt chromium, or stainless steel. In certain embodiments, the upper section 105 and the middle section 110 of the shaft 101 may be fabricated as one continuous component 117. In some embodiments, the lower section 115 may be fabricated as a separate component that is attached to the continuous component 117. The attachment of the lower section 115 to the continuous component 117 may create a hermetically sealed environment within the bore 130 of the shaft. In certain embodiments, the lower section 115 is laser-welded to the continuous component 117.

The physical dimensions of the bone screw 100 are generally consistent with the dimensions of screws for insertion in bone that are known in the art. For example, the length 160 may be about 8 to about 100 mm. The outer diameter 165 of the shaft 101, of which the measurement may include the ends of the threads 122 (for example, see FIG. 4), may vary depending on the type of bone in which the screw is being inserted. For example, for insertion in long bones, the screw 100 may have an outer diameter 165 of about 2 mm to about 20 mm, or about 3 mm to about 15 mm, or about 4 mm to about 10 mm. For insertion in vertebrae, the outer diameter 165 may be about 3.5 mm to about 6 mm for cervical vertebrae, and about 4.5 mm to about 9.5 mm for lumbar vertebrae. In some embodiments, the outer diameter 165 may taper at an angle (not shown) of, for instance, about 1 degree or about 10 degrees towards the lower section 115 of the shaft 101. The inner diameter 170 of the shaft 101, of which the measurement may not include the ends of the threads 122 (for example, see FIG. 4), may also taper at an angle (not shown) of, for example, about 1 degree or about 10 degrees towards the lower section 115 of the shaft 101. The length and diameter of bore 130 and magnet 135 may also vary depending on the bone in which the screw 100 is being inserted. For instance, for insertion in the vertebral body of a cervical vertebra or a lumbar vertebra, the length (not shown) of bore 130 may be about 10 mm to about 20 mm, while the diameter (not shown) of bore 130 may be 3 to 5 mm for cervical applications. The length and diameter of magnet 135 may conform to the dimensions of bore 130.

According to embodiments on the invention, bone screw 100 may also include an external textured surface (not shown), which enhances fixation of the bone screw 100 in bone and to aid in screw-bone interface stability. According to certain embodiments, plasma coating of a metal or ceramic may be applied to bone screw 100 to create the external textured surface.

Disc-Shaped Housing

Figure 2:
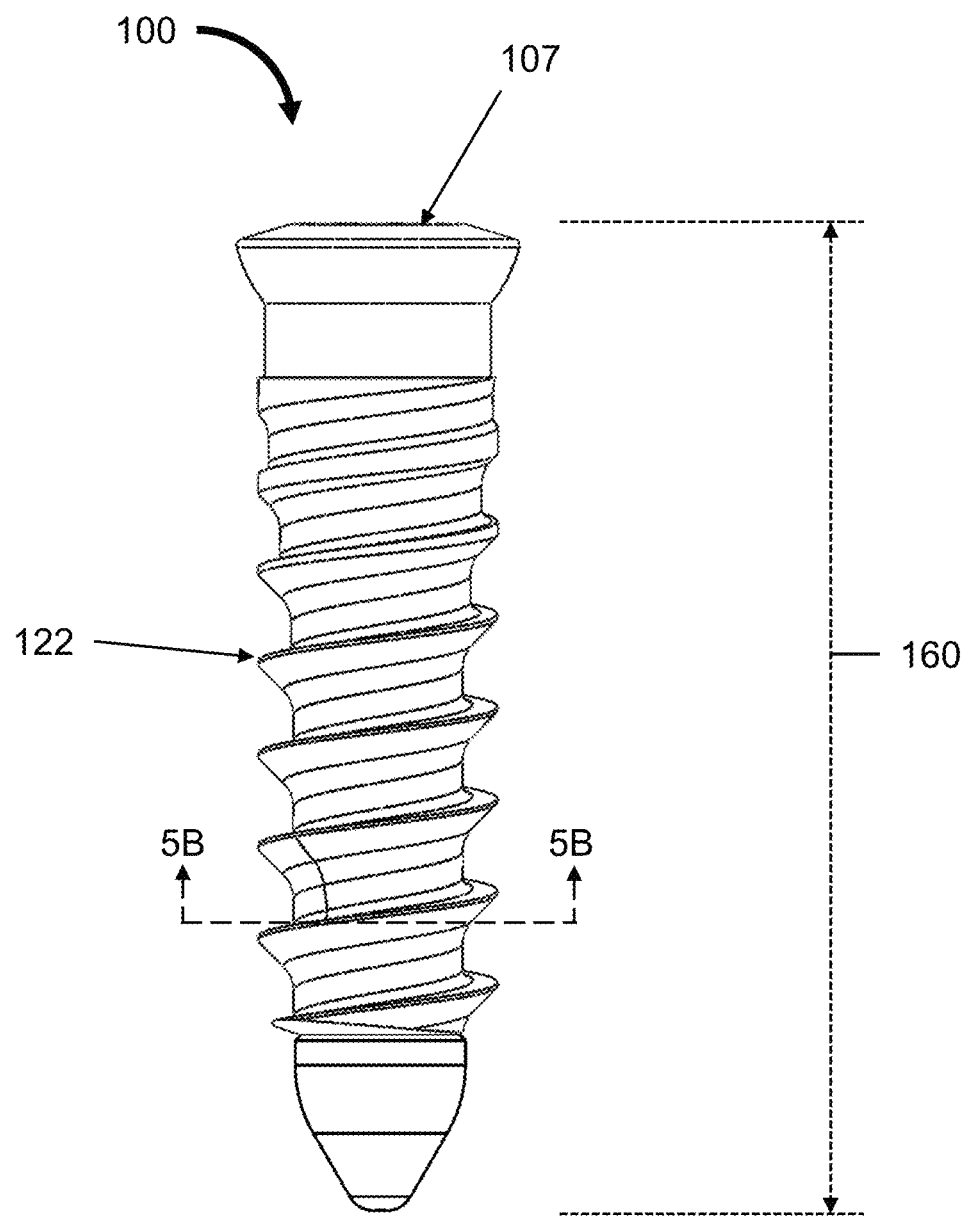
FIG. 2 is a side view of a bone screw according to embodiments of the present invention.
Figure 3:
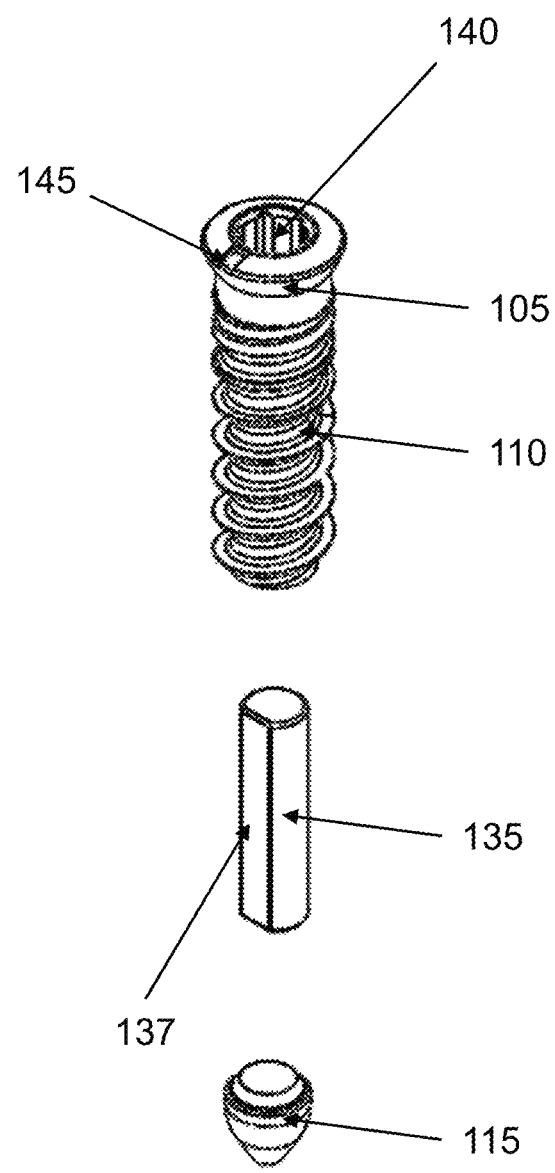
FIG. 3 is an exploded view of a bone screw according to embodiments of the present invention.
Figure 4:
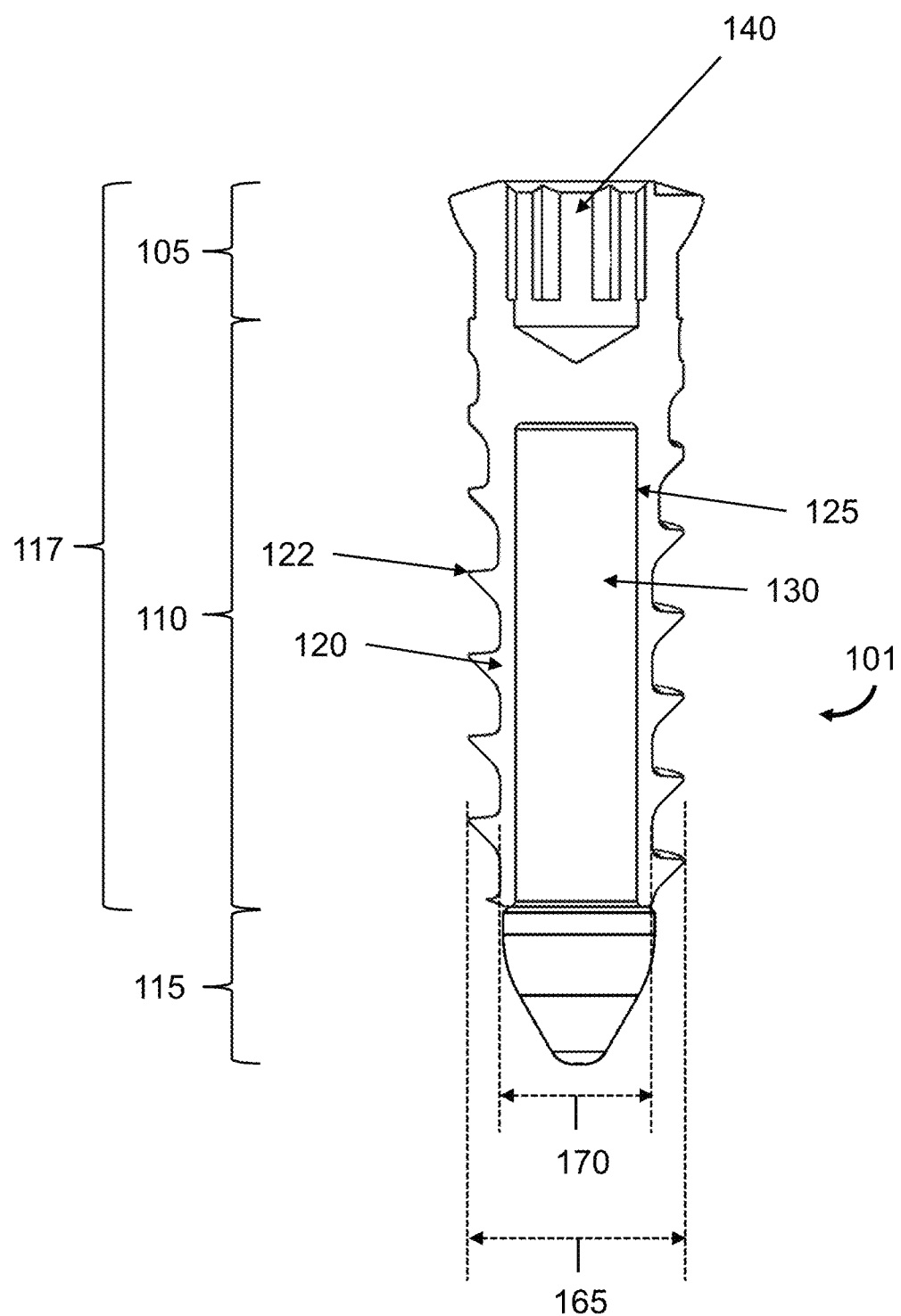
FIG. 4 is a cross-sectional side view of the shaft of a bone screw according to embodiments of the present invention.
Figure 5A:
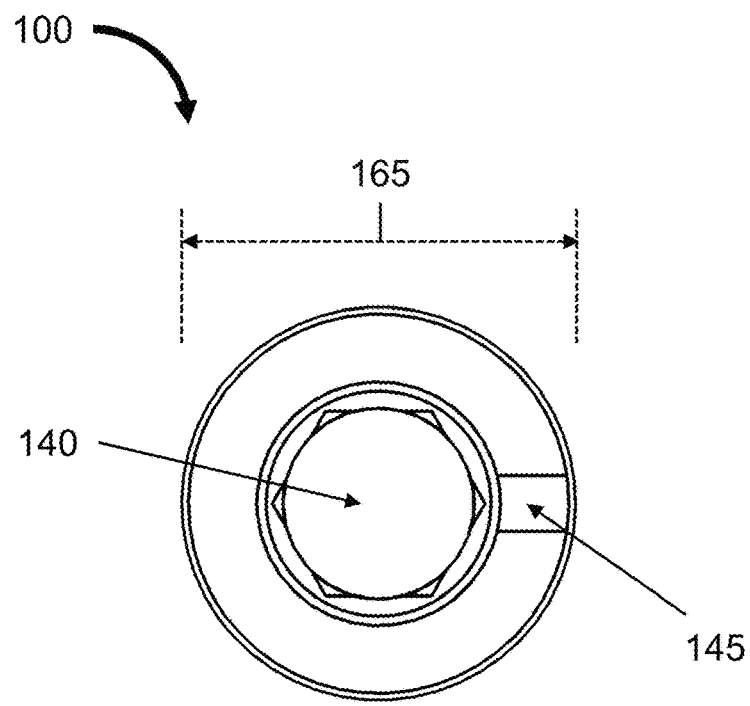
FIGS. 5A and 5B are different views of a bone screw according to embodiments of the present invention.
Figure 5B:
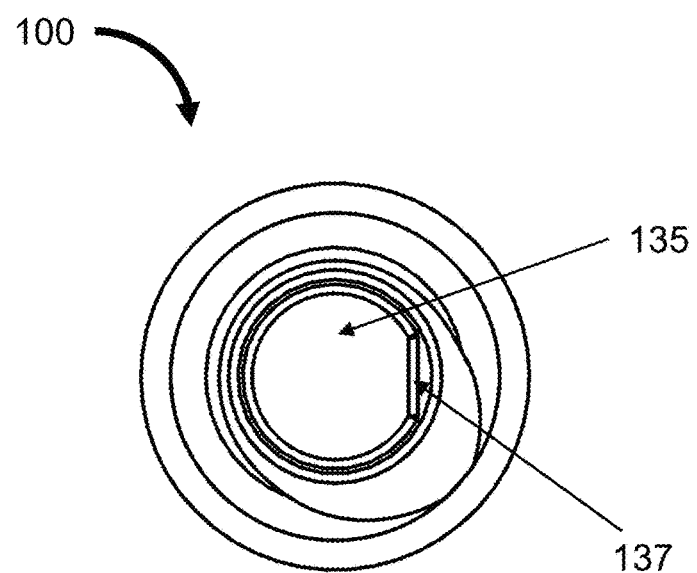
Figure 6A:
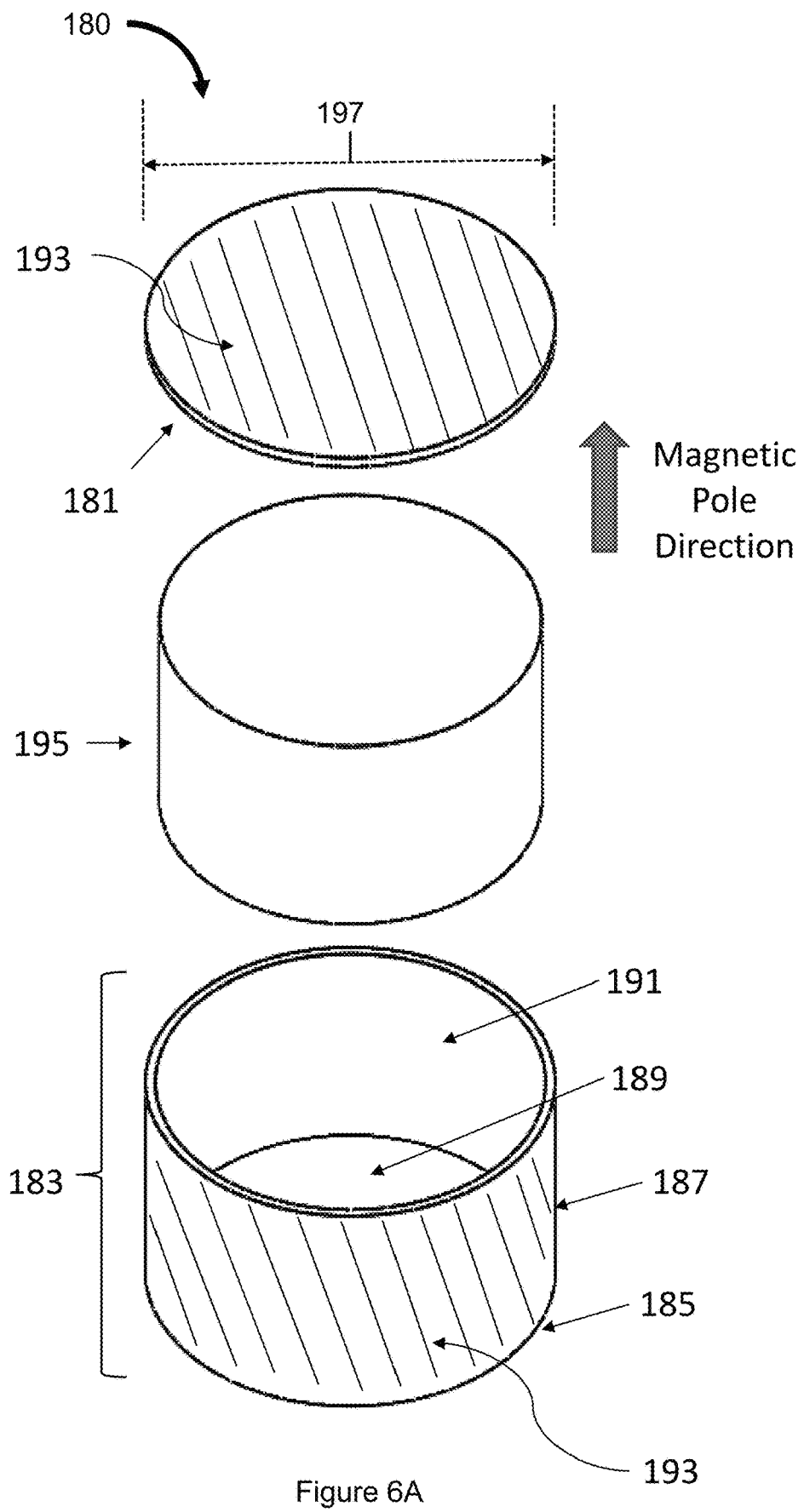
FIGS. 6A and 6B are different views of a disc-shaped housing according to embodiments of the present invention.
Figure 6B:
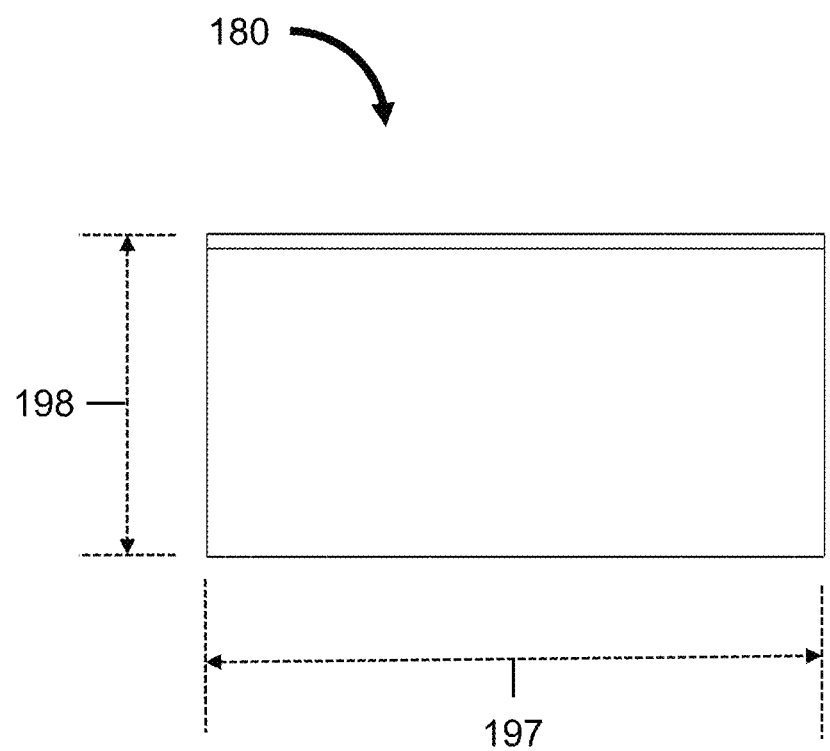

The magnetic device may comprise a disc-shape. In some embodiments, the magnetic device may comprise a disc-shaped housing. With reference to FIGS. 6A and 6B, in certain embodiments, disc-shaped housing 180 may comprise an upper section 181 and a lower section 183. The disc-shaped housing 180 may comprise a cross-section that is generally circular.

The lower section 183 comprises (i) a base 185, (ii) an outer wall surface 187, and (iii) a bore 189 defining an inner wall surface 191. The upper section 181 comprises a cap. The cap has an outer diameter (not shown) approximately equal to the outer diameter (not shown) of outer wall surface 187. The upper section 181 is attached to the lower section 183, for example, by gluing or laser welding, to create a hermetically sealed space. A magnet 195 may be housed in the bore 189, and may be entirely encased within the disc-shaped housing 180 when the upper section 181 is attached to the lower section 183. In certain embodiments, the bore 189 may be generally cylindrical in shape, and therefore the magnet 195 in the bore 189 also may be generally cylindrical in shape. Other shapes are also envisioned for the magnet 195 and the bore 189.

The magnet 195 may be prevented from rotating inside the bore 189. In some embodiments, the magnet 195 may be prevented from rotating inside the bore 189 by gluing or laser welding the magnet 195 to one or more portions of the inner wall surface 191 of the disc-shaped housing 180. For example, the magnet may be glued in place with a surgical adhesive such as medical grade epoxy.

The magnet 195 may comprise materials known in the art. For example, the magnet 195 may be iron-based, nickel-based, cobalt-based, or an alloy of rare-earth metals. In certain embodiments, the magnet 195 may be a rare-earth magnet, which, in certain embodiments, is NdFeB. The magnet 195 may be magnetized in the axial direction.

The disc-shaped housing 180 may be fabricated with a metal alloy known in the art for orthopaedic applications, for example, titanium, cobalt chromium, or stainless steel. The disc-shaped housing 180 may also include an external textured surface 193, which enhances fixation of the disc-shaped housing 180 in bone and to aid in housing-bone interface stability. According to some embodiments, plasma coating of a metal or ceramic is applied to disc-shaped housing 180 to create the external textured surface.

The physical dimensions of disc-shaped housing 180 may vary according to an individual patient's anatomy and the particular bone into which the disc-shaped housing 180 is to be implanted. For example, for implantation in a femur or tibia, the disc-shaped housing 180 may comprise an outer diameter 197 of about 8 mm to about 40 mm, or about 12 mm to about 30 mm, and a height 198 of about 2 mm to about 15 mm, or about 3 mm to about 10 mm. For implantation in vertebrae, the disc-shaped housing may comprise an outer diameter 197 of about 3 mm to about 30 mm, or about 6 mm to about 20 mm, and a height 198 of 2 mm to about 10 mm, or about 3 to about 5 mm.

Use of the Magnetic Devices in a Knee Joint

In one aspect, the methods of the present invention comprise implanting one or more magnetic devices into the femur and one or more magnetic devices into the tibia. The magnetic devices may be oriented such that a repulsive force is generated between the magnetic device(s) in the femur and the magnetic device(s) in the tibia. The implantation may comprise preparing one or more bores in the femur and one or more bores in the tibia for each of the magnetic devices that are being implanted, and then affixing the magnetic devices in the bores in the orientation that results in the repulsive force between the magnetic device(s) in the femur and the magnetic device(s) in the tibia. The bore may comprise a shape that is compatible with the shape of the magnetic device, e.g., a cylindrical bore for implantation of cylindrical magnetic devices, a bore in the shape of a disc or a portion of a disc for implantation of disc-shaped magnetic devices, etc. The bore may be created using a bone drill, bone saw, or other devices known in the art for use in orthopaedic surgeries or procedures.

The magnetic device(s) may be implanted in the distal femur, such as in the lateral condyle or the medial condyle, or both the lateral condyle and the medial condyle. For embodiments in which the magnetic device(s) is implanted in the lateral condyle, the bore(s) may be prepared on the lateral surface, the anterior surface, the posterior surface, or a combination thereof, preferably the lateral surface, of the lateral condyle. For embodiments in which the magnetic device(s) is implanted in the medial condyle, the bore(s) may be prepared on the medial surface, the anterior surface, the posterior surface, or a combination thereof, preferably the medial surface, of the medial condyle.

The magnetic device(s) may be implanted in the proximal tibia, such as in the lateral condyle or the medial condyle, or both the lateral condyle and the medial condyle. For embodiments in which the magnetic device(s) is implanted in the lateral condyle, the bore(s) may be prepared on the lateral surface, the anterior surface, the posterior surface, or a combination thereof, preferably the lateral surface, of the lateral condyle. For embodiments in which the magnetic device(s) is implanted in the medial condyle, the bore(s) may be prepared on the medial surface, the anterior surface, the posterior surface, or a combination thereof, preferably the medial surface, of the medial condyle.

Implanted magnetic devices in the femur and tibia are exemplified in FIGS. 7A-16B. These figures illustrate magnetic device configurations for implantation in a femur 201 having a lateral condyle 203 and a medial condyle 205, along with an anterior surface 207 and a posterior surface 209; and a tibia 211 having a lateral condyle 213 and a medial condyle 215, and an anterior surface 217 and a posterior surface 219. These figures demonstrate magnetic devices that are cylindrical 300, rectangular prism-shaped 350, or disc-shaped 180, or that are bone screws 100 or bone plates 1.

Figure 7A:
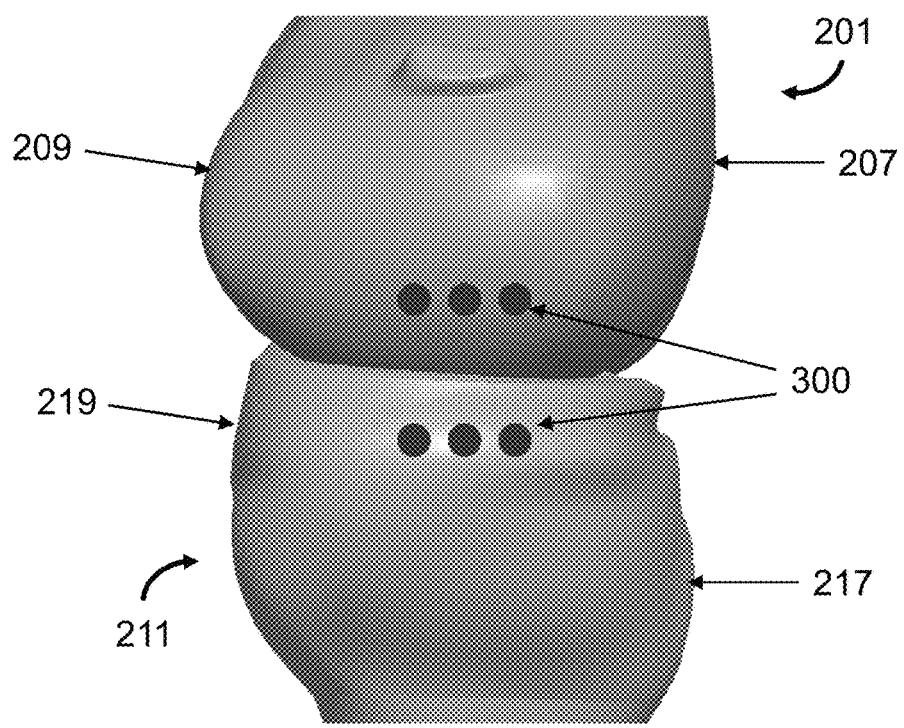
FIGS. 7A and 7B are different views of a knee joint at 0° flexion with cylindrical magnetic devices implanted into the lateral surface of the lateral condyle of the femur and tibia, according to embodiments of the present invention.
Figure 7B:
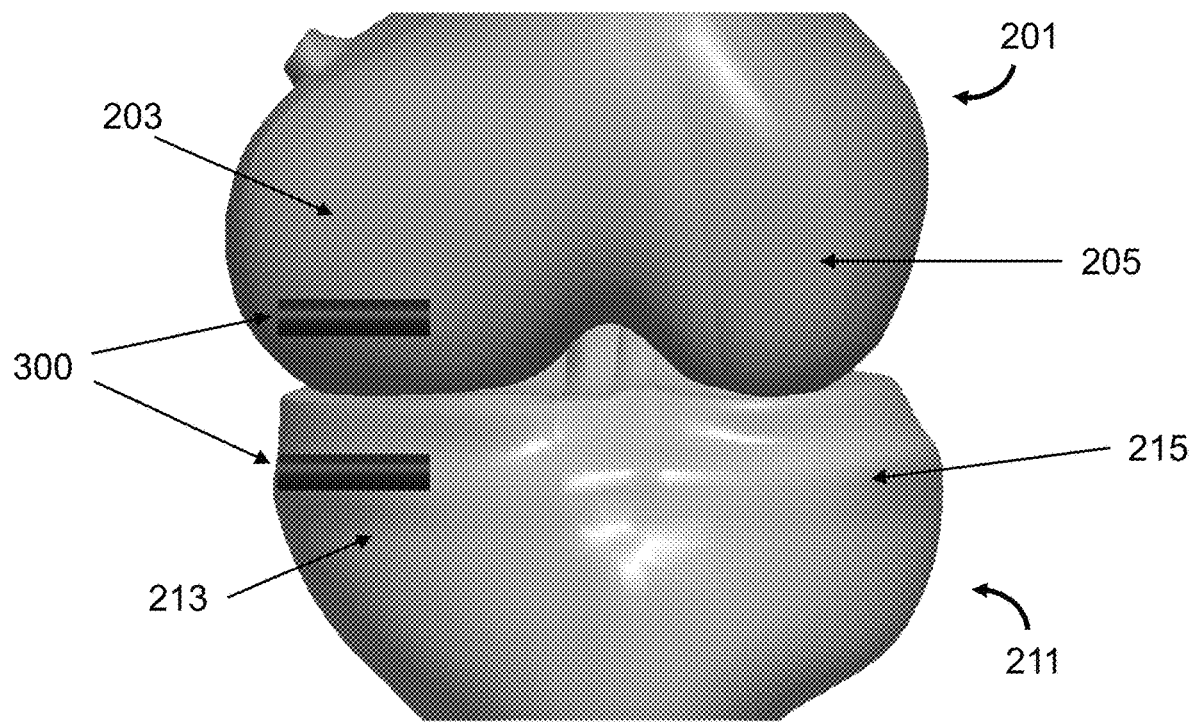

The number of magnetic devices implanted in the femur may range from one to five, e.g., one, two, three, four, or five magnetic devices. In some embodiments, the number of magnet devices implanted in the tibia may range from one to five, e.g., one, two, three, four, or five magnetic devices. The number of magnetic devices implanted in the femur may be the same as the number of magnetic devices implanted in the tibia; such a configuration is illustrated in FIGS. 7A and 7B, in which three cylindrical magnetic devices 300 are implanted into the lateral condyle 203 of the femur 201, and three cylindrical magnetic devices 300 are implanted in the lateral condyle 213 of the tibia 211.

Figure 8A:
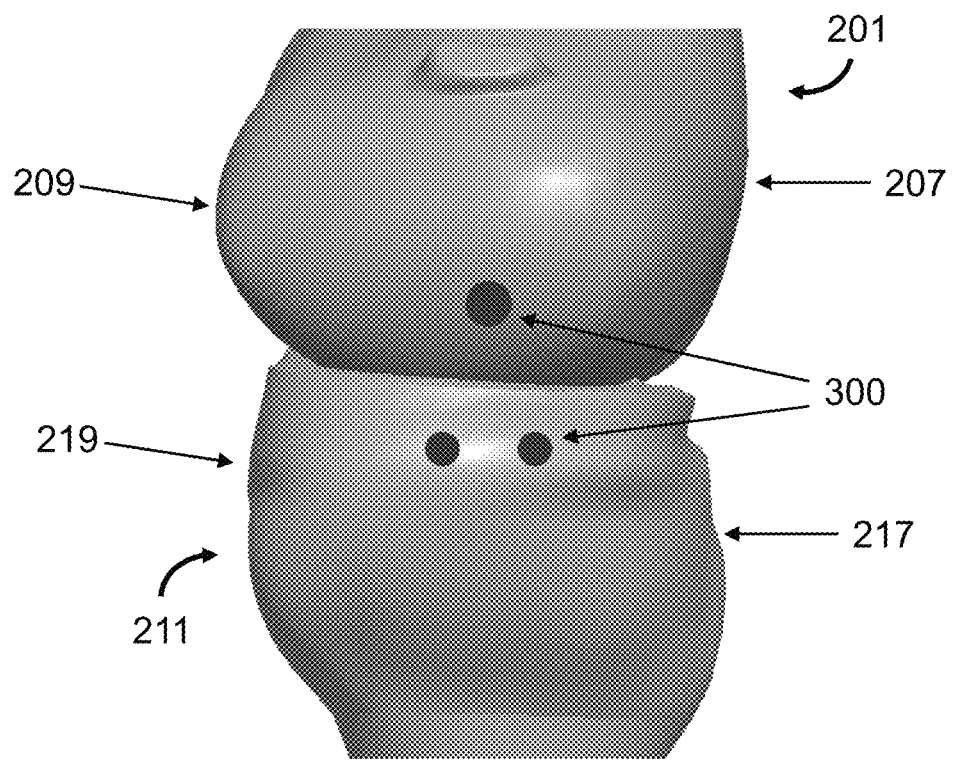
FIGS. 8A and 8B are different views of a knee joint at 0° flexion with cylindrical magnetic devices implanted into the lateral surface of the lateral condyle of the femur and tibia, according to embodiments of the present invention.
Figure 8B:
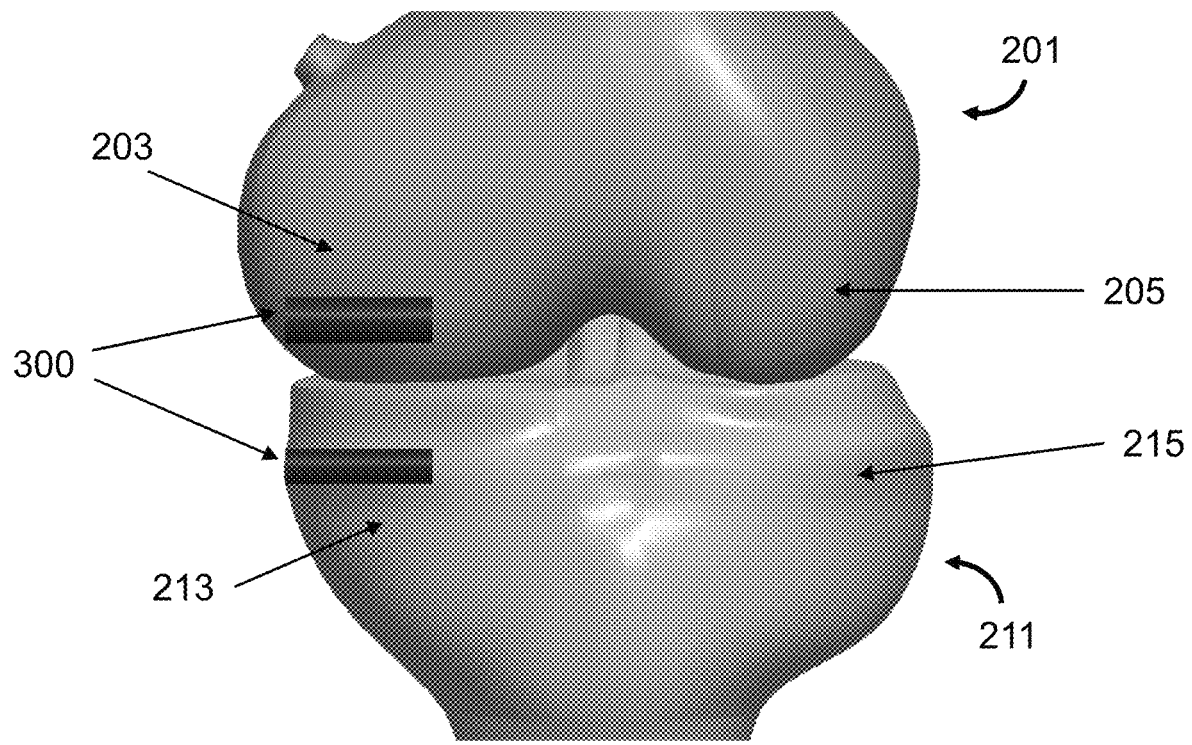
Figure 9A:
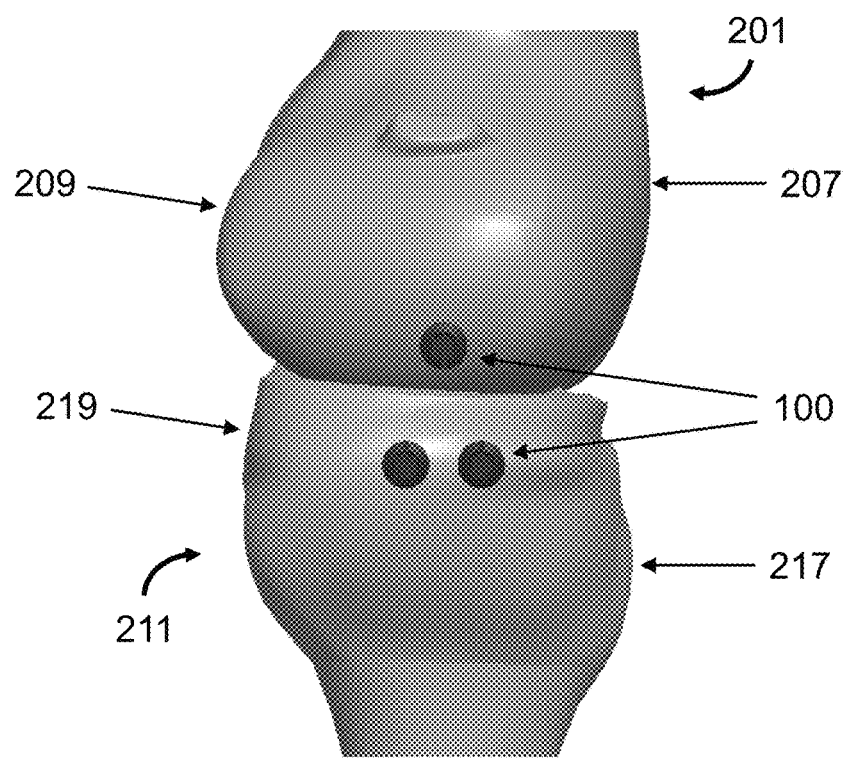
FIGS. 9A and 9B are different views of a knee joint at 0° flexion with bone-screw magnetic devices implanted into the lateral surface of the lateral condyle of the femur and tibia, according to embodiments of the present invention.
Figure 9B:
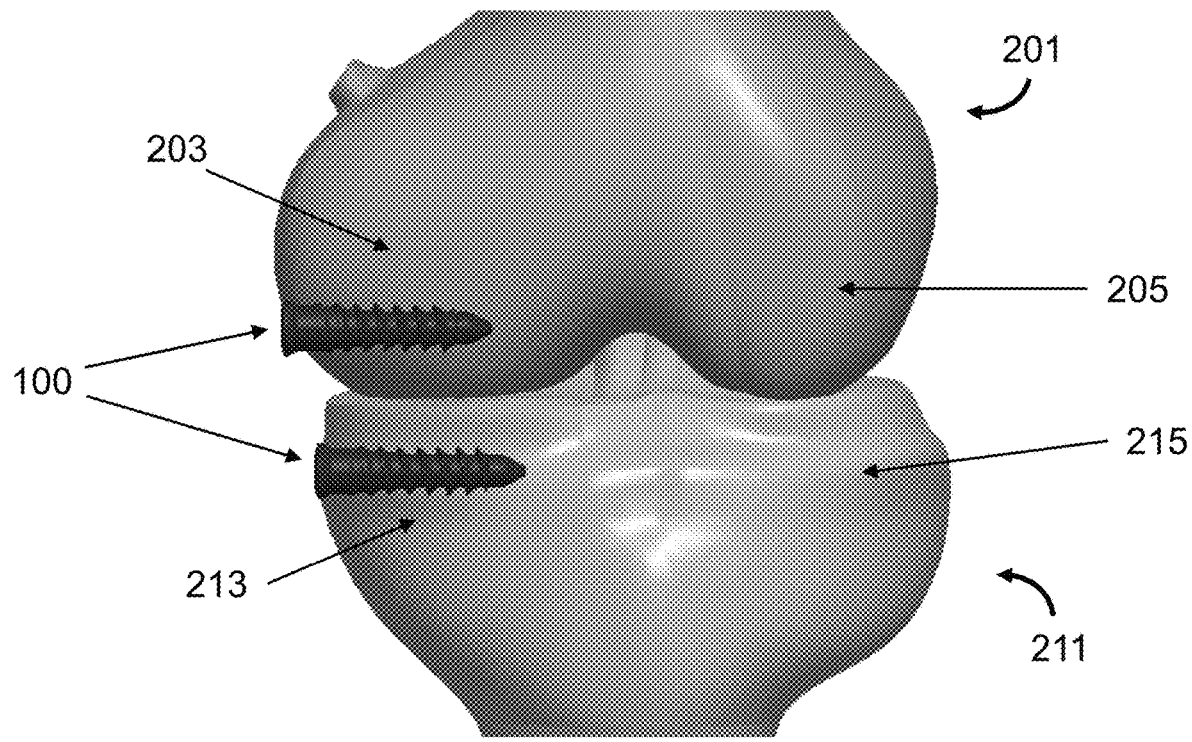
Figure 10A:
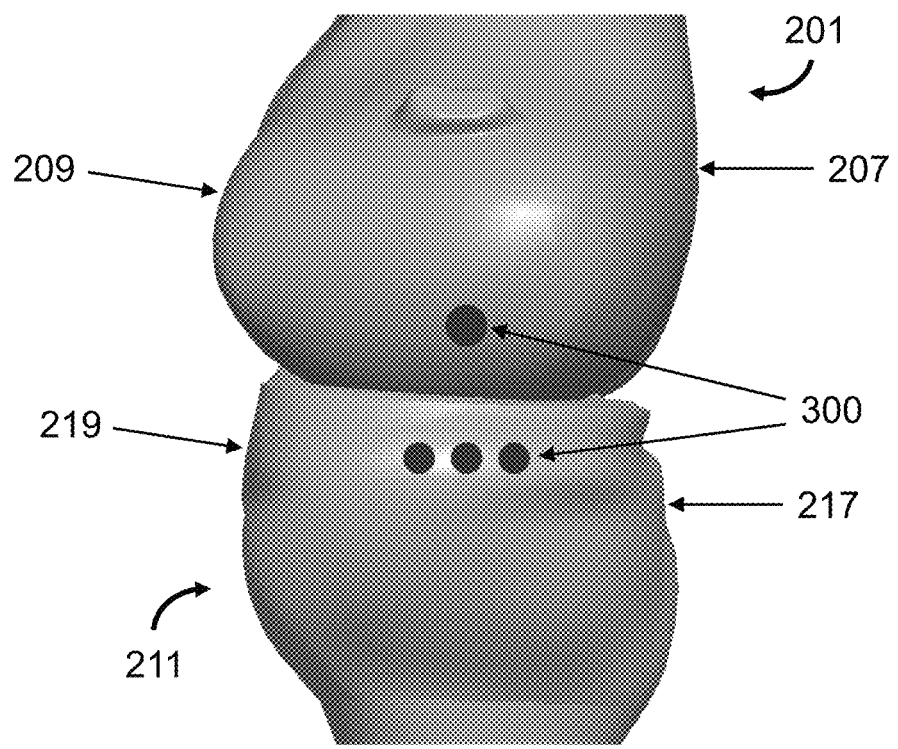
FIGS. 10A and 10B are different views of a knee joint at 0° flexion with cylindrical magnetic devices implanted into the lateral surface of the lateral condyle of the femur and tibia, according to embodiments of the present invention.
Figure 10B:
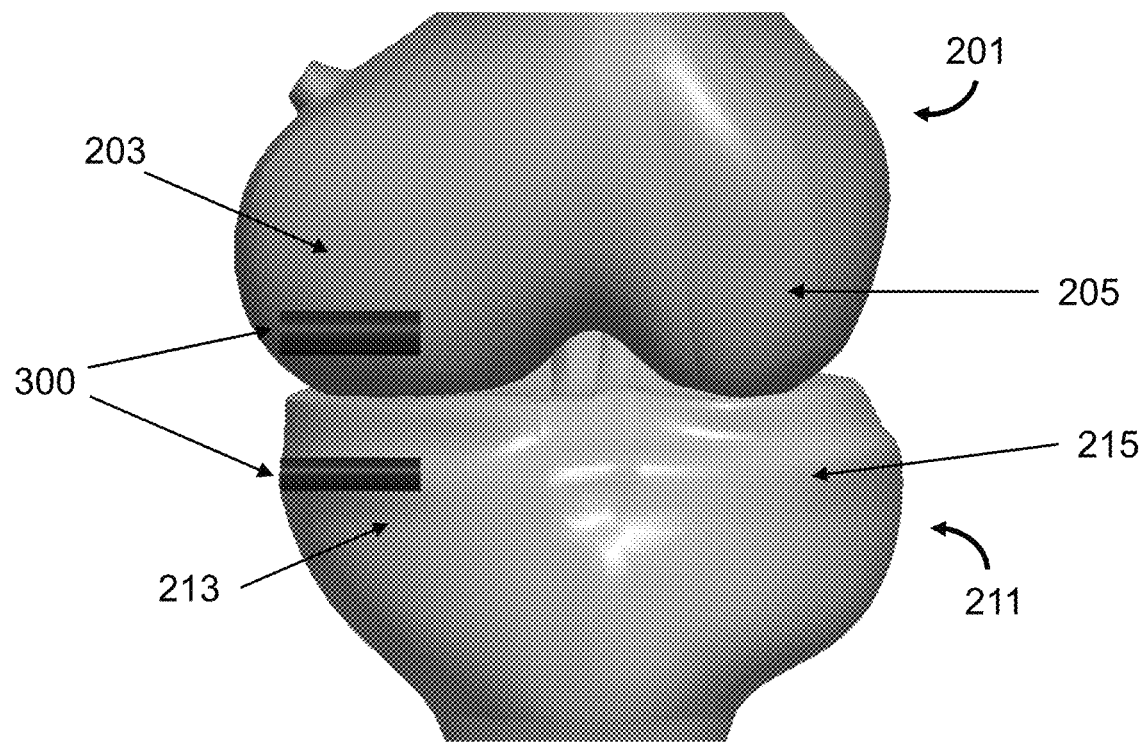

Alternatively, the number of magnets implanted in the femur may be different than the number of magnets implanted in the tibia. FIGS. 8A and 8B show one cylindrical magnetic device 300 implanted into the lateral condyle 203 of the femur 201, and two cylindrical magnetic devices 300 implanted into the lateral condyle 213 of the tibia 211. FIGS. 9A and 9B show one bone-screw magnetic device 100 implanted into the lateral condyle 203 of the femur 201, and two bone-screw magnetic devices 100 implanted into the lateral condyle 213 of the tibia 211. Further, FIGS. 10A and 10B show one cylindrical magnetic device 300 implanted into the lateral condyle 203 of the femur 201, and three cylindrical magnetic devices 300 implanted into the lateral condyle 213 of the tibia 211.

The shape of the magnetic device(s) implanted in the femur may be the same as the shape of the magnetic device(s) implanted in the tibia, as shown in FIGS. 7A, 7B, 8A, 8B, 10A, and 10B, in which the magnetic devices are all cylindrical magnetic devices 300, or as shown in FIGS. 9A and 9B, in which the magnetic devices in both the femur and tibia are bone screws 100. In addition, in FIGS. 11A and 11B, rectangular prism-shaped magnetic devices 350 may be implanted into the lateral condyle 203 of the femur 201 and the lateral condyle 213 of the tibia 211.

The magnetic device(s) implanted in the femur may be a different shape than the magnetic device(s) implanted in the tibia. For instance, as shown in FIGS. 12A and 12B, a cylindrical magnetic device 300 may be implanted into the lateral condyle 203 of the femur 201 and a rectangular prism-shaped magnetic device 350 may be implanted into the lateral condyle 213 of the tibia 211. And as shown in FIGS. 13A and 13B, a cylindrical magnetic device 300 may be implanted into the lateral condyle 203 of the femur 201 and a disc-shaped magnetic device 180 may be implanted into the lateral condyle 213 of the tibia 211.

The magnetic devices are implanted in a configuration such that the one or more magnetic devices of the femur are maintained at a prescribed distance, or a range of distances, from the one or more magnetic devices of the tibia while the knee undergoes motion. The distance may be about 10 mm to about 60 mm, or about 15 mm to about 50 mm. The chosen configuration may also take into account the patient anatomy and the desired level of unloading and stability of the knee joint. For example, if a greater level of unloading is desired, the magnetic devices may be implanted such that they are closer together, or stronger or larger magnets are used.

Figure 11A:
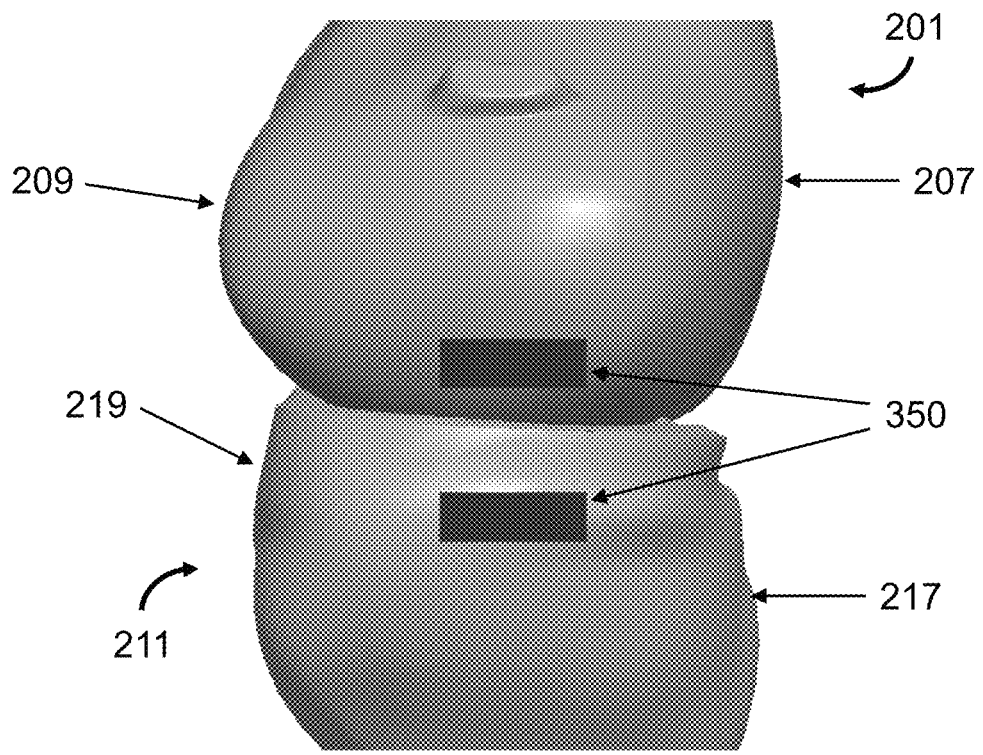
FIGS. 11A and 11B are different views of a knee joint at 0° flexion with rectangular prism-shaped magnetic devices implanted into the lateral surface of the lateral condyle of the femur and tibia, according to embodiments of the present invention.
Figure 11B:
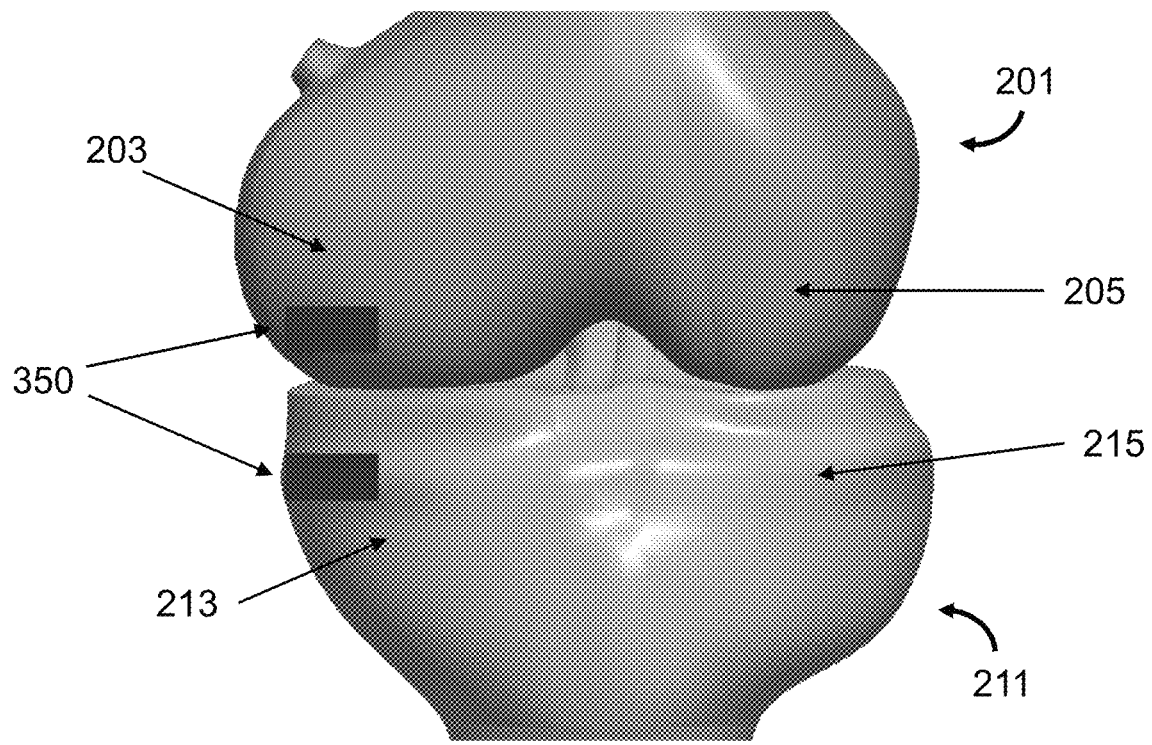

From a side perspective, the magnetic devices may be implanted into the femur and tibia such that the magnetic device(s) in the femur and the magnetic device(s) in the tibia are each in a linear configuration, in which the linear configuration of the magnetic device(s) in the femur is parallel to the linear configuration of the magnetic device(s) in the tibia when the knee is in an extended position, i.e., a flexion angle of 0° (see, e.g., FIGS. 7A, 11A). Alternatively, the magnetic device(s) may be implanted such that the magnetic device(s) in the femur and/or tibia are in a curved configuration. The curved configuration may generally correspond with the curvature of the surface of the bone(s), such as the curvature of the surface of the condyle(s) of the femur or the curvature of the surface of the condyle(s) of the tibia. For example, magnetic device(s) implanted into the lateral surface of the lateral condyle of the femur may be in a configuration that generally corresponds with the anterior-posterior curvature of the distal surface of the lateral condyle of the femur, as depicted in FIGS. 14A-14C and 15A-15C. Magnetic device(s) implanted into the lateral surface of the lateral condyle of the tibia may be in a configuration that generally corresponds with the anterior-posterior curvature of the proximal surface of the lateral condyle of the tibia (not shown). Alternatively or in addition, magnetic device(s) implanted into the medial surface of the lateral condyle of the femur may be in a configuration that generally corresponds with the anterior-posterior curvature of the distal surface of the medial condyle of the femur. Magnetic device(s) implanted into the medial surface of the lateral condyle of the tibia may be in a configuration that generally corresponds with the anterior-posterior curvature of the proximal surface of the medial condyle of the femur and/or tibia. The magnetic device(s) may be implanted at a prescribed distance, or range of distances, from the surface of the bone, in which the distance is measured from magnetic device(s) to the closest point on the bone surface, of about 10 mm to about 60 mm, or about 15 mm to about 50 mm. In some embodiments, the magnetic device(s) implanted in the femur and the magnetic device(s) implanted in the tibia may be in different configurations. For example, the magnetic device(s) implanted in the femur may be in a curved configuration and the magnetic device(s) implanted in the tibia may be in a linear configuration, or vice versa.

FIGS. 14A-14C and 15A-15C illustrate embodiments in which magnetic device(s) 300 implanted in the femur 201 are in a curved configuration and magnetic device(s) 300 (FIGS. 14A-14C) or 350 (FIGS. 15A-15C) implanted in the tibia 211 are in a linear configuration. The curved configuration of magnetic devices 300 in the femur 201 generally corresponds with the anterior-posterior curvature of the distal surface 208 of the lateral condyle of femur 201 that is in contact (through cartilage) with the proximal surface 218 of the lateral condyle of tibia 211.

The linear configuration of magnetic devices may be achieved by using two or more magnetic devices, such as two or more cylindrical magnetic devices 300 (see, e.g., FIGS. 7A, 14A-14C) or two or more bone screw magnetic devices 100 (see, e.g., FIG. 9A), or the linear configuration may be achieved by using a single magnetic device, such as a rectangular prism magnetic device 350 (see, e.g., FIGS. 11A, 12A, 15A-15C) or a disc-shaped magnetic device 180 (see, e.g., FIG. 13A). The curved configuration of magnetic devices may be achieved by using two or more magnetic devices, such as two or more cylindrical magnetic devices 300 (see FIGS. 14A-14C, 15A-15C) or two or more bone screw magnetic devices 100, or the curved configuration may be achieved by using a single magnetic device that is curved in shape (not shown).

In some embodiments, the magnetic device(s) in the femur will be centered in an anterior-posterior direction with the magnetic device(s) in the tibia.

In another aspect, the methods of the present invention may involve attaching magnetic device(s) to the surface of the femur and the tibia. For instance, the magnetic devices may be attached to the surface of the lateral condyle of the femur and of the tibia. Without being bound by theory, the plates can generate a greater repulsive force, because the external magnets can be placed closer to each other relative to the anatomically-constrained distances of those placed within the femur and the tibia.

These methods may comprise affixing magnetic device(s) to the surface of the femur and affixing magnetic device(s) to the surface of the tibia, and orienting the magnetic devices such that a repulsive force is generated between the magnetic device(s) affixed to the femur and the magnetic device(s) affixed to the tibia. The magnetic devices may be affixed to the bone surfaces using bone screws, bone cement, or other means of adhering devices to bone surfaces that are known in the art. Once affixed to the surface of the femur and tibia, the magnetic device(s) may be covered by the soft tissues and skin of the knee.

The magnetic device(s) affixed to the surface of the femur and tibia may be a magnetic device 1 comprising a plate 3 with a casing 5 that encases the magnet, as described above and as shown in FIGS. 1A, 1B, and 1C. These plates affixed to the surface of the femur and tibia is illustrated in FIGS. 16A and 16B, which shows the plate-like magnetic device 1 attached to the lateral condyle 203 of the femur 201 and a plate-like magnetic device 1 attached to the lateral condyle 213 of the tibia 211. The magnets and the casing that encases them may be rectangular (as shown in FIGS. 1A, 1B, and 1C) or, alternatively, may be curved or shaped as an arc (not shown) so that the distance between the magnet of the plate affixed to the femur and the magnet of the plate affixed to the tibia is generally constant; this distance may be about 2 mm to about 30 mm, or about 5 mm to about 25 mm.

Use of the Magnetic Devices in an Acetabulofemoral Joint

In one aspect, the methods of the present invention comprise implanting one or more magnetic devices in the femur and one or more magnetic devices in the hip bone to reduce loading across the acetabulofemoral joint. The magnetic devices may be oriented such that a repulsive force is generated between the magnetic device(s) of the femur and the magnetic device(s) of the hip bone. The implantation may comprise preparing one or more bores in the femur and one or more bores in the hip bone for each of the magnetic devices that are being implanted, and then affixing the magnetic devices in the bores in the orientation that results in the repulsive force. The bore may comprise a shape that is compatible with the shape of the magnetic device, e.g., a cylindrical bore for implantation of cylindrical magnetic devices, a bore in the shape of a disc or a portion of a disc for implantation of disc-shaped magnetic devices, etc. The bore may be created using a bone drill, bone saw, or other devices known in the art for use in orthopaedic surgeries or procedures.

For implantation in the femur, the magnetic device(s) may be implanted in the proximal femur, such as in the femoral head. For implantation in the hip bone, the magnetic device(s) may be implanted adjacent to the acetabulum.

The number of magnetic devices implanted in the femur and the hip bone may each range from one to five, e.g., one, two, three, four, or five magnetic devices. The number of magnetic devices implanted in the femur may be the same as the number of magnetic devices implanted in the hip bone, or the number of magnets implanted in the femur may be different than the number of magnets implanted in the hip bone. Further, the shape of the magnetic device(s) implanted in the femur may be the same or different than the shape of the magnetic device(s) implanted in the hip bone.

The magnetic devices are implanted in a configuration such that the one or more magnetic devices of the femur are maintained at a prescribed distance, or a range of distances, from the one or more magnetic devices of the hip while the acetabulofemoral joint undergoes motion. The chosen array may also take into account the patient anatomy and the desired level of unloading and stability of the acetabulofemoral joint. In some embodiments, the magnetic devices may be implanted such that the magnetic device(s) in the femur and the magnetic device(s) in the hip bone are each in a linear configuration, in which the linear configuration of the magnetic device(s) in the femur is parallel to the linear configuration of the magnetic device(s) in the hip bone. Alternatively, the magnetic device(s) may be implanted such that the magnetic device(s) in the femur and/or hip bone are in a curved configuration. The curved configuration may generally correspond with the curvature of the surface of the bone(s), such as the curvature of the femoral head of the femur or the curvature of the acetabulum of the hip bone. In certain embodiments, the magnetic device(s) in the femur and the magnetic device(s) in the hip bone are in different configurations; for instance, the magnetic device(s) in the femur may be in a curved configuration while the magnetic device(s) in the hip bone are in a linear configuration, or vice versa.

Use of the Magnetic Devices in an Ankle Joint

In one aspect, the methods of the present invention comprise implanting one or more magnetic devices in the distal tibia and/or fibula and one or more magnetic devices in the talus, wherein the one or more magnetic devices in the tibia and/or fibula and the one or more magnetic devices in the talus are oriented to generate a repulsive magnetic force therebetween. In some embodiments, one or more magnetic devices are implanted in both the tibia and the fibula. In other embodiments, one or more magnetic devices are implanted in the tibia only. In certain embodiments, one or more magnetic devices are implanted in the proximal talus.

In one aspect, the methods of the present invention involve implanting one or more magnetic devices in the tibia and/or fibula, and one or more magnetic devices in the talus to reduce loading across the ankle joint. The magnetic devices may be oriented such that a repulsive force is generated between the magnetic device(s) of the tibia and/or fibula, and the magnetic device(s) of the talus. The implantation may comprise preparing one or more bores in the tibia and/or fibula, and one or more bores in the talus for each of the magnetic devices that are being implanted, and then affixing the magnetic devices in the bores in the orientation that results in the repulsive force. The bore may comprise a shape that is compatible with the shape of the magnetic device, e.g., a cylindrical bore for implantation of cylindrical magnetic devices, a bore in the shape of a disc or a portion of a disc for implantation of disc-shaped magnetic devices, etc. The bore may be created using a bone drill, bone saw, or other devices known in the art for use in orthopaedic surgeries or procedures.

For implantation in the tibia and/or fibula, the magnetic device(s) may be implanted in the distal tibia and/or fibula. The magnetic devices may be implanted in the tibia only, the fibula only, or both the tibia and the fibula. For implantation in the talus, the magnetic device(s) may be implanted in the proximal talus. The magnetic devices may be implanted into the lateral surface of the tibia and/or fibula, and the lateral surface of the talus. Alternatively, the magnetic devices may be implanted into the medial surface of the tibia and/or fibula, and the medial surface of the talus. In some embodiments, the magnetic devices may be implanted into both the lateral and medial surfaces of the tibia and/or fibula, and both the lateral and medial surfaces of the talus.

The number of magnetic devices implanted in the tibia and/or fibula and in the talus may each range from one to five, e.g., one, two, three, four, or five magnetic devices. The number of magnetic devices implanted in the fibula and/or tibia may be the same as the number of magnetic devices implanted in the talus, or the number of magnets implanted in the tibia and/or fibula may be different than the number of magnets implanted in the talus. If the magnetic device(s) are implanted in both the tibia and the fibula, the number of magnetic devices implanted in the tibia may be the same or different than the number of magnetic devices implanted in the fibula. Further, the shape of the magnetic device(s) implanted in the tibia and/or fibula may be the same or different than the shape of the magnetic device(s) implanted in the talus. If the magnetic device(s) are implanted in both the tibia and the fibula, the shape of the magnetic device(s) implanted in the tibia may be the same or different than the shape of the magnetic device(s) implanted in the fibula.

The magnetic devices are implanted in a configuration such that the one or more magnetic devices of the tibia and/or fibula are maintained at a prescribed distance, or a range of distances, from the one or more magnetic devices of the talus while the ankle joint undergoes motion. The chosen array may also take into account the patient anatomy and the desired level of unloading and stability of the ankle joint. In some embodiments, the magnetic devices may be implanted such that the magnetic device(s) in the tibia and/or fibula and the magnetic device(s) in the talus are each in a linear configuration, in which the linear configuration of the magnetic device(s) in the tibia and/or fibula is parallel to the linear configuration of the magnetic device(s) in the talus. Alternatively, the magnetic device(s) may be implanted such that the magnetic device(s) in the tibia and/or fibula, and/or in the talus are in a curved configuration. The curved configuration may generally correspond with the curvature of the surface of the bone(s), such as the anterior-posterior curvature of the distal surface of the tibia and/or fibula or the anterior-posterior curvature of the proximal surface of the talus. In certain embodiments, the magnetic device(s) in the tibia and/or fibula and the magnetic device(s) in the talus are in different configurations; for instance, the magnetic device(s) in the tibia and/or fibula may be in a curved configuration while the magnetic device(s) in the talus are in a linear configuration, or vice versa.

Use of the Magnetic Devices in the Intervertebral Joint

In one aspect, the methods of the present invention comprise implanting one or more magnetic devices in a first vertebra that is superior to an intervertebral joint and one or more magnetic devices in a second vertebra that is inferior to an intervertebral joint to reduce loading across the intervertebral joint. The magnetic devices may be oriented such that a repulsive force is generated between the magnetic device(s) of the first vertebra and the magnetic device(s) of the second vertebra bone.

The implantation of the magnetic device(s) in the first vertebra and in the second vertebra may exert a traction force on the vertebrae, such as a consistent, continuous, low magnitude traction force that can maintain disc height and health and relieves acute and chronic neck pain. Implantation of the magnetic device(s) in the first vertebra and in the second vertebra may also treat pain caused by a herniated disk between the first vertebra and the second vertebra, and/or it may treat a herniated disk between the first vertebra and the second vertebra. In certain embodiments, implantation of the magnetic device(s) in the first vertebra and in the second vertebra may relax soft tissue and separate spine vertebral segments by imparting magnetic force(s) to separate and levitate cervical spine segments.

The implantation may comprise preparing one or more bores in the first vertebra and one or more bores in the second vertebra for each of the magnetic devices that are being implanted, and then affixing the magnetic devices in the bores in the orientation that results in the repulsive force. The bore may comprise a shape that is compatible with the shape of the magnetic device, e.g., a cylindrical bore for implantation of cylindrical magnetic devices, a bore in the shape of a disc or a portion of a disc for implantation of disc-shaped magnetic devices, etc. The bore may be created using a bone drill, bone saw, or other devices known in the art for use in orthopaedic surgeries or procedures.

The magnetic device(s) may be implanted in the vertebral body of the first vertebra and in the vertebral body of the second vertebra. In some embodiments, the bore to implant the magnetic devices may be prepared on the anterior surface of the vertebral bodies.

Implanted magnetic devices in vertebrae are exemplified in FIGS. 17A, 17B, 18A, and 18B. These figures illustrate a plurality of bone screws 100/100' and disc-shaped housings 180/180' implanted in the vertebral body 405 of a first vertebra 400 and in the vertebral body 415 of a second, adjacent vertebra 410, according to certain embodiments of the invention.

In certain embodiments of the invention, bone screws 100 and bone screws 100' are inserted in each of vertebral bodies 405 and 415, respectively, of vertebrae 400 and 410, respectively. The marks 145 are used to orient the bone screws 100/100' such that the polarities of the magnets within the bone screws 100/100' generate a repulsive force between the magnets (not shown in FIG. 17A or 17B) of the bone screws 100 and the magnets (not shown in FIG. 17A or 17B) of the bone screws 100' fastened to vertebrae 400 and 410, respectively.

The number of magnetic devices implanted in the vertebrae range from one to five, e.g., one, two, three, four, or five magnetic devices. According to embodiments of the invention, and as demonstrated in FIGS. 17A and 17B, two bone screws 100 may be implanted in vertebral body 405 of vertebra 400 such that their longitudinal centers are separate by a distance 407. The distance 407 can vary depending upon the individual anatomy of the patient. For example, distance 407 can be about 8 mm to about 12 mm. Two bone screws 100' are also implanted in vertebral body 415 of vertebra 410 such that their longitudinal centers are separate by a distance 417. The distance 417 can vary depending upon the individual anatomy of the patient. According to certain embodiments, distance 417 is greater than distance 407. For example, distance 417 can be about 10 mm to about 20 mm. Having distance 417 greater than distance 407 reduces destabilizing anterior-posterior and medial-lateral forces on vertebrae 400 and 410 created by the magnetic forces of the bone screws 100 and the bone screws 100'. Additionally, vertical distance 420 separating the bone screws 100 implanted in vertebral body 405 of vertebra 400 and the bone screws 100 implanted in vertebral body 415 of vertebra 410 may be about 8 mm to about 12 mm.

According to these embodiments, and based upon computer modeling, the repulsive magnetic forces between the magnets (not shown in FIG. 17A or 17B) of the bone screws 100 implanted in vertebral body 405 of vertebra 400 and the magnets (not shown in FIG. 17A or 17B) of the bone screws 100' implanted in vertebral body 415 of vertebra 410 may be about 2 N to about 10 N. According to some embodiments, the repulsive magnetic force is about 5 N. In this configuration, destabilizing anterior-posterior and medial-lateral forces on vertebrae 400 and 410 may be about 1 N or less.

In certain embodiments, and as shown in FIGS. 18A and 18B, disc-shaped housings are inserted in each of vertebral bodies 405 and 415 of vertebrae 400 and 410, respectively. According to these embodiments, a first disc-shaped housing 180 is implanted in vertebral body 405 of vertebra 400. A second disc-shaped housing 180' is implanted in vertebral body 415 of adjacent vertebra 410. According to a preferred embodiment, the outer diameter 197 of disc-shaped housing 180 may be about 6 mm to about 15 mm. The outer diameter 197' of disc-shaped housing 180' is larger than diameter 197. For example, outer diameter 197' of disc-shaped housing 180' may be about 8 mm to about 20 mm. Having diameter 197' larger than diameter 197 reduces destabilizing anterior-posterior and medial-lateral forces on vertebrae 400 and 410 created by the magnetic forces of the disc-shaped housings. Additionally, vertical distance 425 separating the disc-shaped housing 180 implanted in vertebral body 405 of vertebra 400 and the disc-shaped housing 180' implanted in vertebral body 415 of vertebra 410 may be about 8 mm to about 16 mm.

According to these embodiments, and based upon computer modeling, the repulsive magnetic forces between the magnet (not shown in FIG. 18A or 18B) of the disc-shaped housing 180 implanted in vertebral body 405 of vertebra 400 and the magnet (not shown in FIG. 18A or 18B) of the disc-shaped housing 180' implanted in vertebral body 415 of vertebra 410 may be about 2 to about 10 N. According to certain embodiments the repulsive magnetic force is about 5 N. In this configuration, destabilizing anterior-posterior and medial-lateral forces on vertebrae 400 and 410 may be about 1 N or less.

EXAMPLES

Example 1

Modeling was used to study the impact on repulsion force of the size of the magnetic device, separation distance (distance between the magnetic device(s) in a first bone of the joint and the magnetic device(s) in a second bone of the joint), and the depth of the magnetic device (distance that the magnetic device extends into the bone, in some instances the length of the magnetic device). The magnetic forces were modeled using JMAG®, a simulation technology that utilizes finite element analysis to calculate the magnetic forces and fields.

Table 1 below provides examples of repulsion forces generated from particular magnetic devices in certain arrangements. These examples show how changing the separation height can impact the repulsion force.

TABLE 1

Repulsion forces generated from magnetic device(s) implanted in a first bone and a second bone of a joint, as determined using modeling.

| Magnetic Devices | Knee Flexion Angle | Magnet Depth | Separation Height | Repulsion Force |
|---|---|---|---|---|
| A cylindrical magnetic device in the first bone and a disc-shaped magnetic device in the second bone (see, e.g., FIGS. 13A and 13B)<br>Magnetic device of the first bone:<br>Diameter = 6.35 mm<br>Length = 12.7 mm<br>Magnetic device of the second bone:<br>Diameter = 12.7 mm<br>Height = 6.35 mm | 0°<br>0° | 12.7 mm<br>12.7 mm | 15 mm<br>20 mm | 3.0 N<br>1.1 N |
| Three identical cylindrical magnetic devices in the first bone and three identical cylindrical magnetic devices in the second bone (see, e.g., FIGS. 7A and 7B)<br>Magnetic devices of the first bone:<br>Diameter = 4.76 mm<br>Length = 12.7 mm<br>Distance between each device = 2.38 mm<br>Magnetic devices of the second bone:<br>Diameter = 4.76 mm<br>Length = 12.7 mm<br>Distance between each device = 2.38 mm | 0°<br>0° | 12.7 mm<br>12.7 mm | 15 mm<br>20 mm | 3.5 N<br>1.9 N |
| Three identical cylindrical magnetic devices in the first bone and two identical cylindrical magnetic devices in the second bone (see, e.g., FIGS. 14A-14C)<br>Magnetic devices of the first bone:<br>Diameter = 4.76 mm<br>Length = 12.7 mm<br>Distance between each device = 7.94 mm<br>Magnetic devices of the second bone:<br>Diameter = 4.76 mm<br>Length = 12.7 mm<br>Distance between each device = 7.94 mm | 0°<br>45°<br>90° | 12.7 mm<br>12.7 mm<br>12.7 mm | 15 mm<br>15 mm<br>15 mm | 1.59 N<br>1.0 N<br>1.59 N |
| A rectangular prism magnetic device in the first bone and a rectangular prism magnetic device in the second bone (see, e.g., FIGS. 11A and 11B)<br>Magnetic device of the first bone:<br>Length = 12.7 mm<br>Width = 19.05 mm<br>Height = 6.35 mm<br>Magnetic device of the second bone:<br>Length = 12.7 mm<br>Width = 19.05 mm<br>Height = 6.35 mm | 0°<br>0° | 12.7 mm<br>12.7 mm | 15 mm<br>20 mm | 13.0 N<br>5.8 N |
| A plate with a casing that encases a magnetic device in the first bone, and a plate with a casing that encases a magnetic device in the second bone (see, e.g., FIGS. 18A and 18B)<br>Magnetic device of the first bone:<br>Length of plate = 12.7 mm<br>Width of plate = 19.05 mm<br>Height of plate = 6.35 mm<br>Length of protrusion = 12.7 mm<br>Width of protrusion = 19.05 mm<br>Height of protrusion = 6.35 mm<br>Magnetic device of the second bone:<br>Length of plate = 12.7 mm<br>Width of plate = 19.05 mm<br>Height of plate = 6.35 mm<br>Length of protrusion = 12.7 mm<br>Width of protrusion = 19.05 mm<br>Height of protrusion = 6.35 mm | 0°<br>0° | 12.7 mm<br>12.7 mm | 2.5 mm<br>15 mm | 41.8 N<br>13.0 N |

Example 2

A series of finite element analyses were conducted using JMAG to study the magnetic forces that are generated when magnets are used in a cervical traction application. In these studies, four magnets are placed in a configuration depicted in FIGS. 19A and 19B. These magnets are 5 mm in diameter and 20 mm in length. The lower two magnets are 10 mm apart and the upper two magnets are 8 mm apart. The height difference between the upper and lower magnets is varied at 8, 10, and 12 mm.

The analyses determined the repulsion force that was created by the magnets in this configuration. The axial loads generated when the height difference between the upper and lower magnets is 8 mm, 10 mm, and 12 mm are provided in Tables 2, 3, and 4, respectively. These distances are the minimum axial distances for the example given; therefore, the axial loads that are generated represent the maximum axial forces. Values could be changed depending on the patient, for example, the anatomical dimensions of the patient's vertebrae.

TABLE 2

Axial loads generated when the height difference between the upper and lower magnets is 8 mm.

| Magnet | X-Force (N) | Y-Force (N) | Z-Force (N) |
|---|---|---|---|
| Upper Left | −4.8499 | 5.7862 | 0.0051 |
| Upper Right | 4.8245 | 5.7942 | −0.0275 |
| Lower right | 6.4334 | −5.7086 | −0.0429 |
| Lower left | −6.5100 | −5.8269 | −0.0238 |

TABLE 3

Axial loads generated when the height difference between the upper and lower magnets is 10 mm.

| Magnet | X-Force (N) | Y-Force (N) | Z-Force (N) |
|---|---|---|---|
| Upper Left | −6.2114 | 3.0589 | −0.0518 |
| Upper Right | 6.2109 | 2.9520 | 0.0510 |
| Lower right | 4.9500 | −3.0811 | −0.0345 |
| Lower left | −4.9628 | −3.0309 | −0.0041 |

TABLE 4

Axial loads generated when the height difference between the upper and lower magnets is 12 mm.

| Magnet | X-Force (N) | Y-Force (N) | Z-Force (N) |
|---|---|---|---|
| Upper Left | −6.5264 | 2.1109 | −0.0304 |
| Upper Right | 6.5149 | 1.8994 | 0.0233 |
| Lower right | 4.2294 | −1.8929 | −0.0362 |
| Lower left | −4.2380 | −1.9811 | 0.0011 |

The foregoing description is given for clearness of understanding only, and no unnecessary limitations should be understood therefrom, as modifications within the scope of the invention may be apparent to those having ordinary skill in the art.

Detailed embodiments of the present methods and magnetic devices are disclosed herein; however, it is to be understood that the disclosed embodiments are merely illustrative and that the methods and magnetic devices may be embodied in various forms. In addition, each of the examples given in connection with the various embodiments of the systems and methods are intended to be illustrative, and not restrictive.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A method of reducing loading across a knee joint, comprising implanting two or more magnetic devices in the distal femur and one or more magnetic devices in the proximal tibia,
    wherein the two or more magnetic devices implanted in the femur and the one or more magnetic devices implanted in the tibia are oriented to generate a repulsive magnetic force therebetween; and
    wherein the two or more magnetic devices implanted in the distal femur are implanted in a curved configuration that generally corresponds with the curvature of the surface of the distal femur.

2. The method of claim 1, wherein the two or more magnetic devices implanted in the distal femur are implanted in the lateral condyle of the distal femur, and wherein the one or more magnetic devices implanted in the proximal tibia are implanted in the lateral condyle of the proximal tibia.

3. The method of claim 1, wherein the two or more magnetic devices implanted in the distal femur are implanted in the medial condyle of the distal femur, and wherein the one or more magnetic devices implanted in the proximal tibia are implanted in the medial condyle of the proximal tibia.

4. The method of claim 1, wherein the two or more magnetic devices implanted in the distal femur are implanted in a curved configuration that generally corresponds with the curvature of the surface of a condyle of the distal femur.

5. The method of claim 4, wherein the two or more magnetic devices implanted in the distal femur are implanted in a curved configuration that generally corresponds with the curvature of the anterior-posterior surface of a condyle of the distal femur.

6. The method of claim 1, wherein three or more magnetic devices are implanted in the distal femur.

7. The method of claim 1, wherein two or more magnetic devices are implanted in the proximal tibia.

8. The method of claim 7, wherein the two or more magnetic devices implanted in the proximal tibia are implanted in a curved configuration that generally corresponds with the curvature of the surface of the proximal tibia.

9. The method of claim 8, wherein the two or more magnetic devices implanted in the proximal tibia are implanted in a curved configuration that generally corresponds with the surface of a condyle of the proximal tibia.

10. The method of claim 9, wherein the two or more magnetic devices implanted in the proximal tibia are implanted in a curved configuration that generally corresponds with the curvature of the anterior-posterior surface of a condyle of the proximal tibia.

11. The method of claim 1, wherein the two or more magnetic devices implanted in the distal femur and the one or more magnetic devices implanted in the proximal tibia each comprise a magnet having a shape of a cylinder, disc, or rectangular prism.

12. The method of claim 11, wherein the two or more magnetic devices implanted in the distal femur each comprise a magnet having a different shape than the magnet of each of the one or more magnetic devices implanted in the proximal tibia.

13. The method of claim 11, wherein the two or more magnetic devices implanted in the distal femur each comprise a magnet having a shape of a cylinder, and wherein one magnetic device is implanted in the proximal tibia and comprises a magnet having a disc shape.

14. The method of claim 11, wherein the two or more magnetic devices implanted in the distal femur each comprise a magnet having the same shape as the magnet of each of the one or more magnetic devices implanted in the proximal tibia.

15. The method of claim 1, wherein the two or more magnetic devices implanted in the distal femur are maintained at a distance of between about 10 mm and about 60 mm from the one or more magnetic devices implanted in the proximal tibia through the range of motion between the femur and the tibia.

16. The method of claim 15, wherein the two or more magnetic devices implanted in the distal femur are maintained at a distance of between about 15 mm and about 50 mm from the one or more magnetic devices implanted in the proximal tibia through the range of motion between the femur and the tibia.

17. A method of reducing pain in a knee joint caused by cartilage damage in the knee, comprising implanting two or more magnetic devices in the distal femur and one or more magnetic devices in the proximal tibia,
wherein the two or more magnetic devices implanted in the distal femur and the one or more magnetic devices implanted in the proximal tibia are oriented to generate a repulsive magnetic force therebetween; and
wherein the two or more magnetic devices implanted in the distal femur are implanted in a curved configuration that generally corresponds with the curvature of the surface of the distal femur.

18. The method of claim 17, wherein the two or more magnetic devices implanted in the distal femur are implanted in a curved configuration that generally corresponds with the curvature of the anterior-posterior surface of a condyle of the distal femur.

19. The method of claim 17, wherein two or more magnetic devices are implanted in the proximal tibia, and wherein the two or more magnetic devices implanted in the proximal tibia are implanted in a curved configuration that generally corresponds with the curvature of the surface of the proximal tibia.

20. The method of claim 19, wherein two or more magnetic devices are implanted in the proximal tibia, and wherein the two or more magnetic devices implanted in the proximal tibia are implanted in a curved configuration that generally corresponds with the curvature of the anterior-posterior surface of a condyle of the proximal tibia.

* * * * *